United States Patent
Loosmore et al.

[11] Patent Number: 6,054,123
[45] Date of Patent: Apr. 25, 2000

[54] HAEMOPHILUS INFLUENZAE DIMETHYLSULPHOXIDE REDUCTASE ENZYME

[75] Inventors: Sheena M. Loosmore, Aurora; Michel H. Klein, Willowdale, both of Canada

[73] Assignee: Connaught Laboratories Limited, North York, Canada

[21] Appl. No.: 08/549,515

[22] Filed: Oct. 27, 1995

[51] Int. Cl.$^7$ .............................. A61K 38/44; C12N 9/02; C12N 15/00; C07H 21/04
[52] U.S. Cl. ...................... 424/94.4; 435/189; 435/252.3; 435/254.11; 435/320.1; 435/325; 435/410; 536/23.1; 536/23.2
[58] Field of Search .................................. 536/23.2, 23.1; 435/240.2, 252.3, 189, 254.11, 325, 410, 320.1, 252.33; 424/94.4

[56] References Cited

PUBLICATIONS

Fleischmann et al. (1995) Whole–genome random sequencing and assembly of *Haemophilus influenzae* Rd, Science 269: 496–512, Jul. 1995.
Bilous et al. (1988) Nucleotide sequence of the dmsABC operon encoding the anaerobic dimethylsulfoxide reductase of *Escherichia coli*, Mol. Microbiol. 2 (6): 785–795, Aug. 1988.
Rudinger, J. (1976) Characteristics of the amino acids as components of a peptide hormone sequence, In: Peptide Hormones, Ed. J. A. Parsons, pp. 1–7, Jun. 1976.
Berkowitz et al., (1987) J. Pediatr. 110:509.
Claesson et al., (1989) J. Pediart. 114:97.
Black et al., (1991) Pediatr. Infect. Dis. J. 10:97.
Bluestone, C. (1982) Engl., J. Med 306:1399.
Bilous et al., (1988) J. Bacterial. 170:1511–1518.
Bilous et al., (1888) Molec. Microbiol. 2:785–795.
O'Hagan (1992) Clin Pharmokinet. 22:1.
Ulmer et al., (1993) Curr. Opinion Invest. Drugs. 2 (9):983–989.
Lockhoff et al., (1991) Chem, Int. Ed. Engl. 30:1611.
Harkness et al., 91992) J. Bacteriol. 174:2425.
Crowl et al., (1985) Gene 38:31–38.

*Primary Examiner*—Robert A. Wax
*Assistant Examiner*—Einar Stole
*Attorney, Agent, or Firm*—Sim & McBurney

[57] ABSTRACT

Purified and isolated nucleic acid molecules are provided which encode a dimethylsulfoxide reductase enzyme of a strain of Haemophilus or an individual subunit or a fragment or an analog of the dimethylsulfoxide reductase enzyme. The nucleic acid molecules may be used to produce recombinant dimethylsulfoxide reductase enzyme free of contaminants derived from bacteria normally containing the same for purposes of diagnostics and medical treatment. Furthermore, the nucleic acid molecules may be used in diagnostic applications.

8 Claims, 24 Drawing Sheets

FIG.2A

H. influenzae Eagan dmsABC

```
T A T A C A A A G A T T A T A A T T A A C T C G T T T T A G...
                    10                  20                  30    ...
...T T A T T T T C A A T C T G A C T G T G G G G A A C G A
              40                  50                  60
```

```
    Met Ser Asn Phe Asn Gln Ile Ser Arg...
T A T A A T G A G T A A C T T T T A A T C A A A T A A G T C G...
                    70                  80                  90    ...
    Arg Asp Phe Val Lys Ala Ser Ser Ala Gly
...C C G A G A T T T G T C A A G G C G T C A T C T G C G G G
          100                 110                 120
```

```
Ala Ala Leu Ala Val Ser Asn Leu Thr Leu...
A G C T G C A C T G G C A G T T T C A A A T C T T A C T T T...
                    130                 140                 150    ...
    Pro Phe Asn Val Met Ala Lys Glu Thr Gln
...A C C T T T T C A A T G T A A T G G C T A A A G A G A C A
          160                 170                 180
```

```
Arg Leu Asn Asn Glu Asn Asn Gln Glu Arg Ile...
A C G C C T C A A T G A A A A T A A T C A A G A A C G T A T...
                    190                 200                 210    ...
    Val Trp Ser Ala Cys Thr Val Asn Cys Gly
...T G T T T G G A G T G C T T G T A C A G T A A A C T G T G G
          220                 230                 240
```

FIG.2B

```
Ser Arg Cys Pro Leu Arg Met His Val Lys...
TAGCCGTTGTCCATTACGAATGCACGTAAA...
         250                270
                                   ...Asp Asn Arg Ile Thr Tyr Val Glu Thr Asp
                                   ...AGATAACCGAATCACTTATGTGGAAACCGA
                                           280             290           300

Asn Thr Gly Thr Glu Thr Tyr Asn Leu Asp...
TAATACGGGGACAGAAACATATAATCTTGA...
         310                330
                                   ...His Gln Val Arg Ala Cys Leu Arg Gly Arg
                                   ...TCATCAGGTTCGTGCTTGTCTACGTGGACG
                                           340             350           360

Ser Met Arg Arg Val Tyr Asn Pro Asp...
TTCTATGCGTCGTCGAGTGTATAACCCAGA...
         370                390
                                   ...Arg Leu Lys Tyr Pro Met Lys Arg Ile Gly
                                   ...CCGCTTAAATATCCAATGAAACGTATAGG
                                           400             410           420

Lys Arg Gly Glu Gly Lys Phe Lys Arg Ile...
TAAACGCGGAGAAGGTAAATTCAAACGAAT...
         430                450
                                   ...Ser Trp Asp Glu Ala Leu Thr Glu Ile Ala
                                   ...CAGTTGGGATGAGGCTTTAACTGAAATTGC
                                           460             470           480
```

FIG.2C

```
Tyr Ala Leu Lys Arg Asn Ile Lys Lys Tyr...
ATACGCATTGAAACGCAATATCAAAAAATA...
         490                500               510
                                                    Gly Asn Glu Ser Ile Tyr Leu Asn Tyr Gly
                                                ...TGGCAATGAATCAATTTATTTAAACTATGG
                                                         520               530              540

Thr Gly Thr Leu Gly Gly Thr Met Ala Lys...
TACGGGAACACTCGGTGGCACAATGGCTAA...
         550                560               570
                                                    Ser Trp Pro Pro Ala Ser Thr Met Ile Ala
                                                ...ATCTTGGCCACCTGCATCCACTATGATCGC
                                                         580               590              600

Arg Phe Met Asn Cys Ile Gly Gly Tyr Leu...
TCGTTTTATGAATTGTATTGGTGGATATTT...
         610                620               630
                                                    Asn His Tyr Gly Asp Tyr Ser Thr Ala Gln
                                                ...AAACCATTATGGTGATTACAGCACCGCACA
                                                         640               650              660

Ile Ala Val Gly Leu Asp Tyr Thr Tyr Gly...
AATTGCAGTCGGTTTAGATTATACCTATGG...
         670                680               690
                                                    Gly Gly Trp Ala Leu Gly Asn Gly Met Ala
                                                ...TGGTGGTTGGGCATTGGGAAATGGAATGGC
                                                         700               710              720
```

FIG.2D

```
Asp Ile Glu Asn Thr Lys Leu Ile Val Leu...
TGACATTGAAAACACCAAATTAATAGTGTT...
          730              740          750  ...
              Phe Gly Asn Asn Pro Ala Glu Thr Arg Met
           ...ATTCGGTAATAATCCTGCAGAAACTCGTAT
                  760              770              780

Ser Gly Gly Leu Thr Tyr Cys Ile Glu...
GAGTGGAGGTGGTTTAACTTATTGTATTGA...
          790              800          810  ...
              Gln Ala Lys Ala Arg Ser Asn Ala Lys Met
           ...ACAAGCCAAAGCTCGTTCCAATGCCAAAAT
                  820              830              840

Ile Ile Asp Pro Arg Tyr Asn Asp Thr...
GATTATTATCGATCCTCGTTATAATGATAC...
          850              860          870  ...
              Gly Ala Gly Arg Glu Asp Glu Trp Ile Pro
           ...TGGTGCAGGGCGTGAAGATGAGTGGATCCC
                  880              890              900

Ile Arg Pro Gly Thr Asp Ala Ala Leu Val...
AATTCGTCCGGGACTGATGCAGCCCTTGT...
          910              920          930  ...
              Ala Ala Leu Ala Tyr Val Met Ile Gln Glu
           ...TGCTGCCCTTGCTTATGTAATGATTCAAGA
                  940              950              960
```

FIG.2E

```
Asn Leu Val Asp Gln Pro Phe Leu Asp Lys....        Tyr Cys Val Gly Tyr Asp Glu Lys Thr Leu
AAATCTCGTGGATCAACCTTTCTTAGATAA ...    ...ATATTGTGTTGGTTATGATGAAAAACATT
            970              980          990      1000          1010          1020

Pro Ala Asp Ala Pro Lys Asn Gly His Tyr...         Lys Ala Tyr Ile Leu Gly Tyr Gly Asn Asp
ACCTGCGGATGCCCCTAAAAATGGTCATTA ...    ...TAAAGCCTATATTTTAGGTTATGGTAATGA
           1030           1040        1050         1060          1070          1080

Gly Ile Ala Lys Thr Pro Glu Trp Ala Ala...         Lys Ile Thr Gly Ile Pro Ala Glu Arg Ile
TGGTATCGCTAAAACTCCAGAATGGGCGGC ...    ...TAAAATCACGGGTATTCCGGCGGAGAGAAT
           1090           1100        1110         1120          1130          1140

Ile Lys Leu Ala Arg Glu Ile Glu Ser Thr...         Lys Pro Ala Phe Ile Ser Gln Gly Trp Gly
TATTAAACTCGCACGTGAAATTGAGCAC ...      ...AAAACCTGCCTTTATTTCCCAAGGTTGGGG
           1150           1160        1170         1180          1190          1200
```

FIG.2F

```
Pro  Gln  Arg  Arg  Ser  Asn  Gly  Glu  Leu  Ile...
GCCTCAACGTCGTAGTAATGGAGAATTAAT...
         1210              1220              1230 ....
                                                   Ser  Arg  Ala  Ile  Ala  Met  Leu  Pro  Ile  Leu
                                                   ...CTCTCGTGCCATTGCGATGTTGCCAATCTT
                                                               1240              1250              1260
...

Thr  Gly  Asn  Val  Gly  Ile  His  Gly  Gly  Asn...
AACAGGTAATGTTGGAATTCACGGGGTAA...
         1270              1280              1290 ....
                                                   Thr  Gly  Ala  Arg  Glu  Ser  Ala  Tyr  Ser  Ile
                                                   ...CACTGGTGCACGTGAAAGTGCGTATAGCAT
                                                               1300              1310              1320
...

Pro  Phe  Val  Arg  Met  Pro  Thr  Leu  Lys  Asn....
TCCATTTGTGCGGATGCCAACGCTAAAAAA...
         1330              1340              1350 ....
                                                   Pro  Met  Lys  Ala  Ser  Ile  Pro  Met  Phe  Leu
                                                   ...TCCTATGAAAGCAAGCATTCCAATGTTTTT
                                                               1360              1370              1380
...

Gly  Thr  Asp  Ala  Ile  Ile  Arg  Gly  Thr  Glu....
AGGGACAGATGCAATTATTCGTGGCACAGA...
         1390              1400              1410 ....
                                                   Met  Thr  Ala  Leu  Thr  Asp  Gly  Ile  Arg  Gly
                                                   ...AATGACCGCACTTACAGATGGTATTCGTGG
                                                               1420              1430              1440
...
```

FIG.2G

```
Val Asp Lys Leu Ser Pro Pro Ile Lys Val...
TGTTGATAAATTATCGCCCCCAATTAAAGT....
            1450         1460         1470
                    ...Ile Trp Asn Tyr Ala Ser Asn Cys Leu Ile
                    ...AATTTGGAATTACGCAAGTAACTGTTTGAT
                            1480         1490         1500

Asn Gln His Ala Gln Ile Asn Arg Thr His...
TAATCAACACGCACAAATCAATCGTACTCA....
            1510         1520         1530
                    ...Asp Ile Leu Gln Asp Asp Thr Gln Cys Glu
                    ...CGATATTTTACAAGATGATACGCAATGTGA
                            1540         1550         1560

Met Ile Ile Thr Ile Asp Asn His Met Thr...
AATGATCATTACTATTGATAATCATATGAC....
            1570         1580         1590
                    ...Ser Thr Ala Lys Tyr Ser Asp Ile Leu Leu
                    ...ATCTACTGCCAAATACAGTGATATTTTATT
                            1600         1610         1620

Pro Asp Cys Pro Thr Ser Glu Gln Met Asp...
ACCAGATTGTCCAACTTCAGAACAAATGGA....
            1630         1640         1650
                    ...Phe Ala Leu Asp Ala Phe Val Ser Asn Met
                    ...TTTCGCTTTAGATGCCTTTGTATCCAATAT
                            1660         1670         1680
```

FIG.2H

```
Ala Tyr Val Ile Phe Ala Asp Gln Val Ile...
GGCATATGTCATTTTTGCAGATCAAGTGAT...
        1690              1700              1710
                    Lys Pro Ser Phe Glu Cys Arg Pro Ile Tyr
                 ...CAAACCATCTTTTGAATGTAGACCTATTTA
                              1720              1730              1740

Asp Met Leu Ser Asp Leu Ala Glu Lys Met...
CGATATGTTAAGTGATTTAGCTGAGAAAAT...
        1750              1760              1770
                    Gly Val Lys Glu Lys Phe Thr Glu Gly Arg
                 ...GGGCGTAAAGAAAAATTTACTGAAGGAAG
                              1780              1790              1800

Thr Gln Glu Glu Trp Leu Arg His Ile Tyr...
AACACAAGAAGAATGGTTACGCCATATTTA...
        1810              1820              1830
                    Glu Gln Ser Arg Glu Lys Leu Pro Glu Leu
                 ...TGAGCAATCTCGAGAAAAATTACCTGAATT
                              1840              1850              1860

Pro Thr Phe Glu Glu Phe Arg Gln Gln Gly...
ACCTACTTTTGAAGAATTTAGACAACAAGG...
        1870              1880              1890
                    Ile Phe Lys Lys Val Asp Pro Asn Gly Phe
                 ...TATTTTTAAAAAGTTGATCCTAATGGCTT
                              1900              1910              1920
```

FIG.2I

```
Lys Val Ala Tyr Lys Asp Phe Arg Asp Asn...
TAAAGTTGCATACAAAGATTTCCGTGATAA...
         1930           1940          1950  ...
                     Pro Glu Ala His Pro Leu Lys Thr Pro Ser
                  ...TCCAGAAGCCCATCCACTTAAAACGCCATC
                          1960          1970          1980
Gly Lys Ile Glu Ile Tyr Ser Ser Arg Leu...
TGGCAAAATTGAAATTTATTCTTCTCGTCT...
         1990          2000          2010  ...
                     Ala Glu Ile Ala Lys Thr Trp Lys Leu Ala
                  ...AGCTGAAATAGCAAAAACTTGGAAATTAGC
                          2020          2030          2040
Glu Asp Asp Val Ile His Pro Leu Pro Ile...
AGAAGATGACGTAATTCATCCCTTACCTAT...
         2050          2060          2070  ...
                     His Ala Gln Ser Phe Glu His Tyr Gly Asp
                  ...TCACGCCCAAAGTTTTGAGCATTACGGTGA
                          2080          2090          2100
Pro Leu Met Glu Lys Tyr Pro Leu Gln Leu...
TCCATTAATGGAAAAATATCCGTTACAACT...
         2110          2120          2130  ...
                     Ser Gly Phe His Tyr Lys Ala Arg Thr His
                  ...AAGTGGTTTTCACTATAAAGCGAGAACCCA
                          2140          2150          2160
```

FIG. 2J

```
     Ser Thr Tyr Gly Asn Val Asp Val Leu Lys... Ala Ala Asn Pro Gln Glu Val Trp Met Asn
     TTCAACTTATGGCAATGTGGATGTATTAAA... AGCAGCTAATCCACAAGAAGTTTGGATGAA
                              2170                  2180                  2190           ...         2200                  2210                  2220

Pro Ile Asp Ala Lys Pro Arg Asn Ile Lys... Asn Gly Asp Met Ile Arg Ile Phe Asn Asp
     TCCTATTGATGCAAAACCTCGTAATATTAA... AAATGGCGATATGATTCGTATCTTTAATGA
                              2230                  2240                  2250           ...         2260                  2270                  2280

Arg Gly Glu Val His Ile Asn Val Lys Ile... Thr Pro Arg Ile Ile Pro Gly Val Val Ala
     TCGAGGCGAAGTACATATTAATGTAAAAAT... TACACCCCGTATTATTCCAGGGGTTGTGGC
                              2290                  2300                  2310           ...         2320                  2330                  2340

Leu Ser Glu Gly Ala Trp Tyr Ala Pro Asp... Lys Asp Arg Ile Asp His Ser Gly Cys Ile
     ATTAAGCGAGGGGGCTTGGTATGCACCAGA... TAAAGATCGTATCGATCATTCAGGTTGCAT
                              2350                  2360                  2370           ...         2380                  2390                  2400
```

FIG.2K

```
     Asn Val Leu Thr Thr Gln Arg Pro Ser Pro...          Leu Ala Lys Gly Asn Pro Gln His Ser Asn
T A A T G T A C T T A C G A C A C A A C G C C C A T C A C C....G C T T G C G A A A G G T A A T C C G C A A C A T T C T A A
                        2410                  2420                  2430                  2440                  2450                  2460

Leu Val Gln Val Glu Arg Leu ***                      Met Glu Gln Tyr Gly Phe Tyr Phe A
T T T A G T T C A A G T G G A A C G T T T G T A G G G G G A....T A A T T A T G G A A C A A T A T G G T T T T T A T T T T G
                        2470                  2480                  2490                  2500                  2510                  2520 sp Ser Glu Arg Cys Thr Gly Cys Lys Thr...                ...Cys Glu Leu Ala Cys Lys Asp Tyr Lys Asp L
A T T C T G A A C G T T G C A C A G G C T G T A A A A C T T....G T G A A T T A G C C T G T A A G G A T T A C A A A G A T C
                        2530                  2540                  2550                  2560                  2570                  2580 eu Gly Thr Glu Val Asn Phe Arg Arg Ile...                ...Tyr Glu Tyr Thr Gly Gly Gln Trp Asn Gln G
T T G G C A C A G A A G T C A A T T T T C G T C G T A T T T....A T G A A T A T A C A G G T G G T C A G T G G A A T C A A C
                        2590                  2600                  2610                  2620                  2630                  2640
```

FIG.2L

```
    ln  Ala  Asp  Gly  Cys  Trp  His  Gln  Asn  Ile                                  Phe  Gly  Tyr  Tyr  Met  Ser                         Ile  Ser  Cys  Asn  H
AAGCAGATGGATGCTGGCATCAAAATATAT...                                              ...TTGGTTATTATATGTCTATTTCTTGTAATC
                  2650                              2660                  2670...          2680                  2690                  2700 is  Cys  Ala  Asp  Pro  Ala  Cys  Thr  Lys  Val                                  Cys  Pro  Thr  Gly  Ala  Met                         His  Lys  Asn  Ala  A
ATTGTGCAGATCCTGCTTGTACAAAAGTTT...                                              ...GCCCAACTGGTGCAATGCACAAAAATGCAG
                  2710                              2720                  2730...          2740                  2750                  2760 sp  Gly  Phe  Val  Ile  Val  Asn  Glu  Glu  Ile                                  Cys  Ile  Gly  Cys  Arg  Tyr                         Cys  His  Met  Ala  C
ATGGTTTCGTGATCGTCAATGAAGAAATTT...                                              ...GTATCGGTTGTCGTTATTGTCATATGGCGT
                  2770                              2780                  2790...          2800                  2810                  2820 ys  Pro  Tyr  Asp  Ala  Pro  Gln  Tyr  Asp  Ala                                  Gln  Lys  Gly  His  Met  Thr                         Lys  Cys  Asp  Gly  C
GTCCTTATGATGCACCGCAATATGATGCAC...                                              ...AAAAAGGTCATATGACAAAAATGTGATGGAT
                  2830                              2840                  2850...          2860                  2870                  2880
```

FIG.2M

```
ys  Tyr Ser Arg Val Lys Ser Gly Gln Lys ....
GTTATTCTCGCGTAAAATCAGGTCAAAAAC...
         2890              2900          2910...

Pro Ile Cys Val Asp Ala Cys Pro Leu Arg A
       ...CGATTTGTGTTGATGCCTGCCCACTACGAG
              2920              2930          2940 la  Leu Asp Phe Ala Pro Ile Asp Glu Leu ....
CATTGGATTTCGCTCCTATTGATGAACTTC...
         2950              2960          2970...

Arg Thr Lys Tyr Gly Thr Gln Ala Ser Ile A
       ...GAACAAAATATGGCACACAAGCCTCCATCG
              2980              2990          3000
       ...

la  Pro Leu Pro Pro Thr Asp Ile Thr Gln ....
CACCACTACCACCGACTGATATCACTCAAC...
         3010              3020          3030...

Pro Asn Leu Val Lys Pro Asn Lys Tyr A
       ...CAAATTTAGTGGTAAAACCAATAAATACG
              3040              3050          3060 la  Arg Leu Ser Gly Asp Thr Ser Gly Phe ....
CTCGTTTAAGTGGCGATACAAGTGGGTTCT...
         3070              3080          3090...

Leu Gly Asn Pro Arg Glu Val *** Met Asn
       ...TAGGAAACCCAAGAGAGGTGTAAGATGAAT
              3100              3110          3120
       ...
```

FIG.2N

```
Thr Gly Leu Tyr Glu Leu Pro Leu Val Phe ....
ACAGGATTATATGAACTGCCATTAGTATTT....
         3130              3140              3150....

Phe Thr Val Leu Ala Gln Ser Ala Ala Gly
   ...TTTACAGTTTGGCACAAAGTGCGGCCGGT
              3160              3170              3180

Ala Trp Leu Val Phe Thr Phe Val Leu Leu ....
GCTTGGCTTGTTTTCACATTTGTACTATTA....
         3190              3200              3210....

Asn Glu Lys Asn Thr Lys Ser Arg Thr Tyr
   ...AATGAGAAAAATACAAAAGTCGCACTTAT
              3220              3230              3240

Ile His Lys Val Met Phe Val Ile Leu Ala ....
ATTCATAAAGTAATGTTTGTGATTTTGGCT....
         3250              3260              3270....

Leu Leu Gly Ile Gly Phe Ile Ala Ser Ile
   ...TTACTAGGTATTGGATTTATTGCTTCCATT
              3280              3290              3300

Met His Leu Gly Leu Pro Ile Arg Ala Phe ....
ATGCATCTTGGCTTACCTATACGTGCATTT....
         3310              3320              3330....

Asn Ser Leu Asn Arg Val Gly Ser Ser Met
   ...AATTCACTTAATCGAGTCGGCTCATCAATG
              3340              3350              3360
```

FIG. 20

Met Ser Asn Glu Ile Ala Ala Gly Ala Ile ...
ATGAGTAATGAAATTGCCGCTGGTGCAATA...
        3370                3380                3390...

Phe Phe Thr Leu Ala Gly Phe Tyr Trp Leu
            ...TTTTTCACATTAGCAGGTTTCTACTGGCTG
                        3400                3410             3420

Ile Ala Ile Leu Gly Lys Met Pro Val Ser ...
ATTGCAATTTTAGGTAAAATGCCAGTTTCA...
        3430                3440                3450...

Leu Gly Asn Val Trp Arg Ile Val Thr Ala
            ...CTTGGAAATGTATGGCGAATTGTGACCGCC
                        3460                3470             3480

Leu Ile Gly Ile Leu Phe Met Tyr Val Met...
CTTATCGGCATACTATTTATGTATGTAATG...
        3490                3500                3510...

Asn Gln Val Tyr His Ile Thr Ser Ile Pro
            ...AATCAGGTTTACCATATTACAAGCATACCA
                        3520                3530             3540

Thr Trp Asn Asn Ala Leu Thr Ser Trp Ser....
ACTTGGAATAATGCATTAACCTCTTGGTCA...
        3550                3560                3570....

Phe Tyr Leu Thr Val Leu Gly Gly Leu
            ...TTCTACCTTACCGTTGTATTAGGTGGATTA
                        3580                3590             3600

FIG.2P

```
Thr Leu Ser Tyr Ala Leu Leu Ile Pro Asn...
ACATTGAGCTATGCGTTATTAATCCCTAAT...
      3610              3620              3630....
                    Lys Gln Arg Glu Tyr Gln Leu Gln His Leu
                ...AAACAACGTGAATATCAGCTTCAGCATCTG
                         3640              3650              3660

Pro Ser Leu Phe Ala Ile Gly Val Ser Leu....
CCAAGTTTATTCGCCATTGGGGTATCATTG....
      3670              3680              3690....
                    Val Ala Ile Val Ala Ile Tyr Gln Gly Phe
                ...GTCGCAATAGTAGCCATATATCAAGGCTTC
                         3700              3710              3720

Asn Leu His Asn Ile His Ser Ala Ile Gln....
AATTTACACAATATTCACAGTGCTATTCAA....
      3730              3740              3750....
                    Asn Ala Ala Asp Leu Val Pro Asn Tyr Ala
                ...AATGCCGCTGACCTCGTACCAAATTATGCC
                         3760              3770              3780

Ile Met Thr Val Thr Arg Leu Cys Leu Leu....
ATAATGACCGTAACTCGCTTATGTTTACTT....
      3790              3800              3810....
                    Ser Ile Val Ala Phe Leu Leu Phe Arg Val
                ...TCCATTGTAGCTTTCCTCTTATTCCGAGTG
                         3820              3830              3840
```

FIG.2Q

```
Lys Asn Ile Gly Leu Leu Gly Ile Ser Val ...         Leu Thr Val Ala Glu Gly Ile Gly
AAAACATAGGACTATTAGGTATTTCCGTT... ...CTATTAACGTTAGTAGCTGAAGGCATCGGC
       3850              3860              3870              3880              3890              3900

Arg Val Leu Phe Tyr Gly Leu His Met Thr ...         Tyr Gly Met Ala Ile Gly Gly ***
CGCGTATTATTTTATGGATTACATATGACT... ...TACGGCATGGCGATTGGTGGTTAAATTATG
       3910              3920              3930              3940              3950              3960

TTGAGGCGTATTGCATACGCCCTCAATTTTT... ...AGAAACGTTAATTAGTAATATTTAACCACC
       3970              3980              3990              4000              4010              4020

CCTCATATCCCCATTCACTAATGACAATTGG
       4030              4040              4050
```

Comparison of DmsA from H. influenzae and E. coli

```
MSNFNQISRRDFVKASSAGAALAVSNLTLPFNMAKETQRLNENN-QERIWSACTVNCGSRCPLRM-MKDNRITYVETDNTGTETYNLDHQVRACLRGRS    Hib
........................M.S.A......SRI.HAVDSAIPTKSD.KVI..............V.GE.K...........DDN.DGL.......    E. coli MRRRVYNPDRLKYPMKRIGKRGEGKFKRISMDEALTETAYALKRNIKKYGNESIYLNYGTGTLGTMAKSMPPASTMEARFMNCIGGYLNHYGDYSTAQI    Hib
.............V.A..........E....E..YDI..TNMQ.L.E..................TR....GN.LV.L....C........S......    E. coli AVGLDYTYGGGWALGNGMADIENTKLIVLFGNNPAETRMSGGGLTYCIEQAKARSNAKMIIDPRYNDTGAGREDEWIPIRPGTDAALVAALAYVMIQEN    Hib
.E..N......-..D..SPS.....S.V..........G........V..YL...RQK...R...........T..................NG....T.    E. coli LVDQPFLDKYCVGYDEKTLPADAPKNGHYKAYILGYGNDGIAKTPEWAAKITGIPAERIIKLAREIGSTKPAFISQGWGPQRRSNGELISRAIAMLPILT    Hib
........S..............................................E.P..V......SQ...V..DK...............HA...IAT...S..A...    E. coli GNVGIHGGNTGARESAYSIPFVRMPTLKNPMKASIPMFLGTDAIRGTEMTALTDGIRGVDKLSPPIKVIMNYASNCLINQHAQINRTHDILQDDTQCEM    Hib
..N...S......GS..L.......E..IQT..S..MW......E..P......R..V..K..DV..M......G...........SE.....E.....KK..L    E. coli IITIDNHMTSTAKYSDILLPDCPTSEQMDFALDAFVSNMAYVIFADQVIKPSFECRPTYDMLSDLAEKMGVKEKFTEGRTQEEWLRHIYEQSREKLPELP    Hib
.W....C......S....A...........TA.........SCG..S......N......R....KT..E.T.E..KRL..EQQ............M..L.A.....AI....    E. coli TFEEFRQQGIFKKVDPNGFKVAYKDFRDNPEAHPLKTPSGKIETYSSRLAEIAKTWKLAEDDVIHPLPIHAQSFEHYGDPLMEKYPLQLSGFHYKARTHS    Hib
...........K......R..QGHH....A..ED.Q.N..T...........QA..D..A..E.P.G...D.....YTPG..S.Q....NKQ....T......S.V..    E. coli TYGNMDVLKAANPQEVWMNPIDAKPRNIKNGDMIRIFNDRGEVHINVKITPRIIPGWALSEGAWYAPDKDRIDHSGCINVLTTQRPSPLAKGNPQHSNL    Hib
.........................EA..V.....MM................G....AK..V..KG.................................S..T..    E. coli VQVERL*    Hib
....KV*    E. coli
```

FIG.3

Comparison of DmsB from H. influenzae and E. coli

```
M-EQYGFYFDSERCTGKTCELACKDYKDLGTEVNFRRIYEYTGGQMNQQADGCMHQNIFGYMSISCNHCADPACTKVCPTGAMHKNADGFVTVNEEICI    Hib
.TT....FI..S..........TP..S......A..D.-.EDN.V....V.A..L......E........S......RE....V.D.DV..            E. coli GCRYCHMACPYDAPQYDAQKGHMTKCDGCYSRVKSGQKPICVDACPLRALDFAPIDELRTKYGTQASIAP--LPPTDITQPNLVVKPNKYARLSGDTSGFLG  Hib
........G....NET..........D..AEGK......ES..........G......K.H.DL.AV..RA..RAHF.K.I.I...ANS.PT....T.Y.A  E. coli NPREV*                                                                                                  Hib
..K..*                                                                                                  E. coli
```

FIG.4

Comparison of DmsC from H. influenzae and E. coli

```
MNTGLYELPLVFFTVLAQSAAGAWLVFTFVLL-NEKNTKSRTYIHKVMFVILALLGIGFIASIMHLGLPIRAFNSLNRVGSSMSNEIAAGAIFFTLAGFY     Hib
.GS..WH.W..MI....FG.CV..GFI.LALA..KGDLRAEAQQRVIAC..GLWV.M.......ML...S.M........A.AL......S.S...AVG.IG   E. coli WLIAILGKMPVSLGNWMRIVTALIGILFMYVMNQVYH-ITSIPTWNNALTSWSFYLTWLGGLTLSYALLIPNKQREYQLQHLPSLFAIGVSLVATVAI        Hib
..L.M.K.LSPA.RTL.L...MVL.VI..VWM.VR..NS.DTV...YSIW.PMG.F..MFM..PL.G.L..SLAGVDGWAMRL..AISVLALVVSGV.SV      E. coli YQGFNLHNIHSAIQNAADLVPNYAIMTVTRLCLLSIVAFLLFRVKNIG------LLGISVLLTLVAEGIGRVLFYGLHMTYGWAIGG*                 Hib
M..AE.AT...SV.Q..A...D.GALMSW.IV..AVALC.WIAPQLK.YQPAVP..SV.FI.L.AG.L...GV............VAS*               E. coli
```

FIG.5

H. influenzae DMS A

```
MSNFNQISRRDFVKASSAGAALAVSNLTLPFNMAKETQRLNENNQERIWSACTVNCGSRCPLRMHVKDNRITYVETDNTGTETYNLDHQVRACLRGRS   Eagan
................................................................................................   SB33

MRRRVYNPDRLKYPMKRIGKRGEGKFKRISWDEALTEIAYALKRNIKKYGNESIYLNYGTGTLGGTMAKSWPPASTMIARFMNCIGGYLNHYGDYSTAQI   Eagan
....................................D...............................................................   SB33

AVGLDYTYGGGWALGNGMADIENTKLIVLFGNNPAETRMSGGGLTYCIEQAKARSNAKMIIDPRYNDTGAGREDEWIPIRPGTDAALVAALAYMIQEN   Eagan
...............................................................................................S.   SB33

LVDQPFLDKYCVGYDEKTLPADAPKNGHYKAYILGYGNDGIAKTPEWAAKITGIPAERIIKLAREIGSTKPAFISQQWGPQRRSNGELISRATAMLPILT   Eagan
....................................................................................................   SB33

GNVGIHGGNTGARESAYSIPFVRMPTLKNPMKASIPMFLGTDAIIRGTEMTALTDGIRGVDKLSPPTIKVIMNYASNCLINQHAQINRTHDILQDDTQCEM   Eagan
..............................V............W......................S...............................   SB33

IITIDNHMTSTAKYSDILLPDCPTSEQMDFALDAFVSNMAYVIFADQVIKPSFECRPIYDMLSDLAEKMGVKEKFTEGRTQEEMLRHIYEQSREKLPELP   Eagan
........T...........................................................................................   SB33

TFEEFRQQGIFKKVDPNGFKVAYKDFRDNPEAHPLKTPSGKIETYSSRLAETAKTWKLAEDDVIHPLPIHAQSFEHYGDPLMEKYPLQLSGFHYKARTHS   Eagan
.......................................................G..........................................   SB33

TYGNMDVLKAANPQEVWMNPIDAKPRNIIKNGDMIRIFNDRGEVHINVKITPRIIPGVVALSEGAWYAPDKDRIDHSGCINVLTTQRPSPLAKGNPQHSNL   Eagan
.......V....I...................E..................................S...............................F.   SB33

VQVERL**
.......
```

FIG.6

H. influenzae DMS B

MEQYGFYFDSERCTGCKTCELACKDYKDLGTEVNFRRIYEYTGGQMNQQADGCMHQNIFGYMSISCNHCADPACTKVCPTGAMHKNADGFVIVNEEICI   Eagan SB33
..........................................................A.........................................

GCRYCHMACPYDAPQYDAQKGHMTKCDGCYSRVKSGQKPICVDACPLRALDFAPIDELRTKYGTQASIAPLPPTDITQPNLVVKPNKYARLSGDTSGFLG   Eagan NPREV*   Eagan

FIG.7

HAEMOPHILUS INFLUENZAE DIMETHYLSULPHOXIDE REDUCTASE ENZYME

FIELD OF INVENTION

The present invention is related to the molecular cloning of genes encoding dimethylsulphoxide reductase enzyme and, in particular, to the cloning of dimethylsulphoxide reductase genes from *Haemophilus influenzae*.

BACKGROUND OF THE INVENTION

*Haemophilus influenzae* is responsible for a number of local and invasive diseases in adults and children. There are six serotypes of *H. influenzae* which are defined by their capsular polysaccharide and designated a–f. In children, *H. influenzae* type b (Hib) causes 95 to 96% of invasive disease such as meningitis, epiglottitis and septicemia, and in adults Hib is responsible for 50% of invasive disease. Non-encapsulated or nontypable *H. influenzae* (NTHi) are a major cause of otitis media, bacteremia, chronic bronchitis and pneumonia. Of the other serotypes, *H. influenzae* types a, d, e and f have been associated with invasive disease at low frequencies. Vaccines based upon *H. influenzae* type b capsular polysaccharide conjugated to diphtheria toxoid (Ref. 1, Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure), tetanus toxoid (Ref. 2 and U.S. Pat. No. 4,496,538), or *Neisseria meningitidis* outer membrane protein (Ref. 3) have been effective in reducing *H. influenzae* type b-induced meningitis, but not NTHi-induced disease (Ref. 4).

Otitis media is the most common illness of early childhood with 60 to 70% of all children of less than 2 years of age experiencing between one and three ear infections. Chronic otitis media is responsible for hearing, speech and cognitive impairments in children. *H. influenzae* infections account for about 30% of the cases of acute otitis media and about 60% of chronic otitis media. In the United States alone, treatment of otitis media costs between 1 and 2 billion dollars per year for antibiotics and surgical procedures such as tonsillectomies, adenoidectomies and insertion of tympanostomy tubes. Furthermore, many of the causative organisms of otitis media are becoming resistant to antibiotic treatment. An effective prophylactic vaccine against otitis media is thus desirable. Non-typable strains of *H. influenzae* are also important pathogens responsible for pneumonia in the elderly and other individuals who are particularly susceptible to respiratory infections. There is thus a need for antigens from *H. influenzae* which are useful as components in immunogenic preparations that provide protection against the many serotypes of *H. influenzae*. *Escherichia coli* and *H. influenzae* are both facultative anaerobes. *E. coli* can derive energy for anaerobic growth by anaerobic respiration, utilizing substrates such as fumarate, nitrate, trimethylamine N-oxide (TMAO) and dimethylsulphoxide (DMSO). The anaerobic growth of *E. coli* on DMSO, TMAO, fumarate or methionine sulphoxide results in the induction of a membrane-bound molybdoenzyme catalysing the reduction of DMSO to dimethylsulphide (Ref. 5). The *E. coli* dimethylsulfoxide reductase enzyme is a complex of three proteins, namely DMS A, DMS B, and DMS C. The 87.4 kDa DMS A protein is the catalytic subunit which contains the non-covalently bound molybdopterin co-factor. The 23.1 kDa DMS B subunit is involved in electron transport and has homology to the (4Fe-4S) ferredoxins. The hydrophobic 30.8 kDa DMS C subunit anchors the complex in the cytoplasmic membrane. The *E. coli* dimethylsulphoxide reductase protein complex is encoded on an operon, dmsABC (Ref. 6). It would be desirable to provide the sequence of the DNA molecule that encodes a dimethylsulfoxide reductase enzyme of a strain of Haemophilus or an individual subunit or a fragment or an analog of the dimethylsulfoxide reductase enzyme and vectors containing such sequences for diagnosis, immunization and the generation of diagnostic and immunological reagents.

SUMMARY OF THE INVENTION

The present invention is directed towards the provision of purified and isolated nucleic acid molecules encoding a dimethylsulfoxide reductase enzyme of a strain of Haemophilus or a fragment or an analog of the dimethylsulfoxide reductase enzyme. The nucleic acid molecules provided herein are useful for the specific detection of strains of Haemophilus, and for diagnosis of infection by Haemophilus. The purified and isolated nucleic acid molecules provided herein, such as DNA, are also useful for expressing the dimethylsulfoxide reductase enzyme by recombinant DNA means for providing, in an economical manner, purified and isolated dimethylsulfoxide reductase enzyme subunits, fragments or analogs thereof. The dimethylsulfoxide reductase enzyme, subunits or fragments thereof or analogs thereof, as well as nucleic acid molecules encoding the same and vectors containing such nucleic acid molecules, are useful in immunogenic compositions against diseases caused by Haemophilus, the diagnosis of infection by Haemophilus and as tools for the generation of immunological reagents. Monoclonal antibodies or mono-specific antisera (antibodies) raised against the dimethylsulfoxide reductase enzyme produced in accordance with aspects of the present invention are useful for the diagnosis of infection by Haenophilus, the specific detection of Haemophilus (in for example in vitro and in vivo assays) and for the treatment of diseases caused by Haemophilus.

Peptides corresponding to portions of the dimethylsulfoxide reductase, subunit or analogs thereof are useful immunogenic compositions against disease caused by Haemophilus, the diagnosis of infection by Haemophilus and as tools for the generation of immunological reagents. Monoclonal antibodies or antisera raised against these peptides are useful for the diagnosis of infection by Haemophilus, the specific detection of Haemophilus (in, for example, in vitro and in vivo assays) and for use in passive immunization as a treatment of disease caused by Haemophilus.

In accordance with one aspect of the present invention, there is provided a purified and isolated nucleic acid molecule encoding a dimethylsulfoxide reductase enzyme of a strain of Haemophilus, more particularly, a strain of *H. influenzae*, specifically a strain of *H. influenzae* type b, such as *H. influenzae* type b strain Eagan, or a non-typable strain of *H. influenzae*, such as *H. influenzae* strain SB33, or an individual subunit or a fragment or an analog of the dimethylsulfoxide reductase enzyme.

In one preferred embodiment of the invention, the nucleic acid molecule may encode only an individual subunit of dimethylsulfoxide reductase enzyme, which may be subunit A, B or C.

In another aspect of the present invention, there is provided a purified and isolated nucleic acid molecule having a DNA sequence selected from the group consisting of (a) any one of the DNA sequences set out in FIG. 2 (SEQ ID No: 1, 2, 3 and 4), or a complementary DNA sequence thereto; (b) a DNA sequence encoding one of the amino acid sequences set out in FIGS. 2, 6 or 7 (SEQ ID Nos: 5, 6, 7, 11 and 12) or a complementary DNA sequence thereto; and (c) a DNA sequence which hybridizes under stringent conditions to any one of the DNA sequences defined in (a) or (b). The DNA sequence defined in (c) preferably has at least about 90% sequence identity with any one of the DNA sequences defined in (a) and (b).

In an additional aspect, the present invention includes a vector adapted for transformation of a host, comprising a nucleic acid molecule as provided herein and expression means operatively coupled to the nucleic acid molecule for expression by the host of the dimethylsulfoxide reductase enzyme of a strain of Haemophilus or the individual subunit or the fragment or the analog of the dimethylsulfoxide reductase enzyme.

A vector having the characteristics of plasmid JB-1474-1 having ATCC Designation number 97216 also is provided herein.

The plasmids may be adapted for expression of the encoded dimethylsulfoxide reductase enzyme, subunits, fragments or analogs thereof, in a heterologous or homologous host, in either a lipidated or non-lipidated form. The expression means also may include a nucleic acid portion encoding a lipidation signal for expression from the host of a lipidated form of the dimethylsulfoxide reductase enzyme, individual subunit or the fragment or the analog of the dimethylsulfoxide reductase enzyme. The host may be selected from, for example, *Escherichia coli,* Bacillus, Haemophilus, Bordetella, fungi, yeast or baculovirus and Semliki Forest virus expression systems may be used.

In an additional aspect of the invention, there is provided a transformed host containing a vector as provided herein. The invention further includes a recombinant dimethylsulfoxide reductase enzyme or individual subunit or fragment or analog thereof producible by the transformed host.

The present invention further provides synthetic peptides corresponding to portions of the dimethylsulfoxide reductase enzyme. Such synthetic peptides have no less than six amino acids and no more than 150 amino acids and contain an amino acid sequence corresponding to a portion only of dimethylsulfoxide reductase enzyme of a strain of Haemophilus or a subunit of an analog of dimethylsulfoxide reductase enzyme. The Haemophilus strain preferably is a *H. influenzae* strain, specifically a strain of *H. influenzae* type b or a non-typable strain of *H. influenzae.*

In accordance with another aspect of the invention, an immunogenic composition is provided which comprises at least one active component selected from at least one nucleic acid molecule as provided herein and at least one recombinant protein as provided herein, and a pharmaceutically acceptable carrier therefor or vector therefor. The at least one active component produces an immune response when administered to a host.

The immunogenic compositions provided herein may be formulated as a vaccine for in vivo administration to protect against diseases caused by bacterial pathogens that produce dimethylsulfoxide reductase enzyme. For such purpose, the compositions may be formulated as a microparticle, capsule or liposome preparation. Alternatively, the compositions may be provided in combination with a targeting molecule for delivery to specific cells of the immune system or to mucosal surfaces. The immunogenic composition may comprise a plurality of active components to provide protection against disease caused by a plurality of species of dimethylsulfoxide reductase producing bacteria. The immunogenic compositions may further comprise an adjuvant. The adjuvant may be selected from the group consisting of aluminum phosphate, aluminum hydroxide, QS21, Quil A or derivatives or components thereof, calcium phosphate, calcium hydroxide, zinc hydroxide, a glycolipid analog, an octodecyl ester of an amino acid, a muramyl dipeptide, a lipoprotein, polyphosphazene, ISCOM matrix, ISCOPREP, DC-chol, and DDBA.

In accordance with another aspect of the invention, there is provided a method for inducing protection against infection or disease caused by Haemophilus or other bacteria that produce dimethylsulfoxide reductase enzyme, comprising the step of administering to a susceptible host, such as a human, an effective amount of the immunogenic composition as recited above. An antiserum or antibody specific for the recombinant protein, the synthetic peptide or the immunogenic composition, also is provided.

In a further aspect, there is provided a live vector for delivery of dimethylsulfoxide reductase enzyme to a host, comprising a vector containing the nucleic acid molecule as described above. The vector may be selected from Salmonella, BCG, adenovirus, poxvirus, vaccinia and poliovirus.

BRIEF DESCRIPTION OF DRAWINGS

The present invention will be further understood from the following description with reference to the drawings, in which:

FIG. 2 shows the nucleotide sequence of the dmsABC operon (SEQ ID No: 1), the nucleotide sequences of the dmsA, dmsB and dmsc genes (SEQ ID Nos: 2, 3, 4) and the deduced amino acid sequences of the DMS A (SEQ ID No: 5), DMS B (SEQ ID No: 6) and DMS C (SEQ ID No: 7) individual subunits from the *H. influenzae* type b strain Eagan.

FIG. 3 shows a comparison of the amino acid sequences of DMS A from *H. influenzae* type b Eagan and *E. coli.* Dots indicate identical residues and dashes are used for maximal alignment. Stop codons are indicated by asterisks.

FIG. 4 shows a comparison of the amino acid sequences of DMS B from *H. influenzae* type b Eagan and *E. coli.* Dots indicate identical residues and dashes are used for maximal alignment. Stop codons are indicated by asterisks.

FIG. 5 shows a comparison of the amino acid sequences of DMS C from *H. influenzae* type b Eagan and *E. coli.* Dots indicate identical residues and dashes are used for maximal alignment. Stop codons are indicated by asterisks.

FIG. 6 shows a comparison of the amino acid sequences of the complete DMS A subunit from *H. influenzae* type b Eagan and a partial sequence of the *H. influenzae* non-typable SB33 DMS A subunit. Dots indicate identical residues and dashes are used for maximal alignment. Stop codons are indicated by asterisks.

FIG. 7 shows a comparison of the amino acid sequences of the complete DMS B subunit from *H. influenzae* type b Eagan and a partial sequence of the *H. influenzae* non-typable SB33 DMS B subunit. Dots indicate identical residues and dashes are used for maximal alignment. Stop codons are indicated by asterisks.

GENERAL DESCRIPTION OF THE INVENTION

Any Haemophilus strain may be conveniently used to provide the purified and isolated nucleic acid which may be in the form of DNA molecules, comprising at least a portion of the nucleic acid coding for dimethylsulfoxide reductase enzyme as typified by embodiments of the present invention. Such strains are generally available from clinical sources and from bacterial culture collections, such as the American Type Culture Collection.

In this application, the term "dimethylsulfoxide reductase enzyme" is used to define a family of functionally and immunologically related proteins and individual subunits thereof which include those having variations in their various amino acid sequences including those naturally occurring in various strains of Haemophilus. The purified and isolated DNA molecules encoding a dimethylsulfoxide reductase enzyme of a strain of Haemophilus of the present invention also include those encoding functional analogs of the dimethylsulfoxide reductase enzyme. In this application, a first protein peptide is a "functional analog" of a second protein if the first protein is immunologically related to and/or has the same function as the second protein. The functional analog may be, for example, a fragment of the protein or a substitution addition or deletion mutant thereof.

Figure 1:
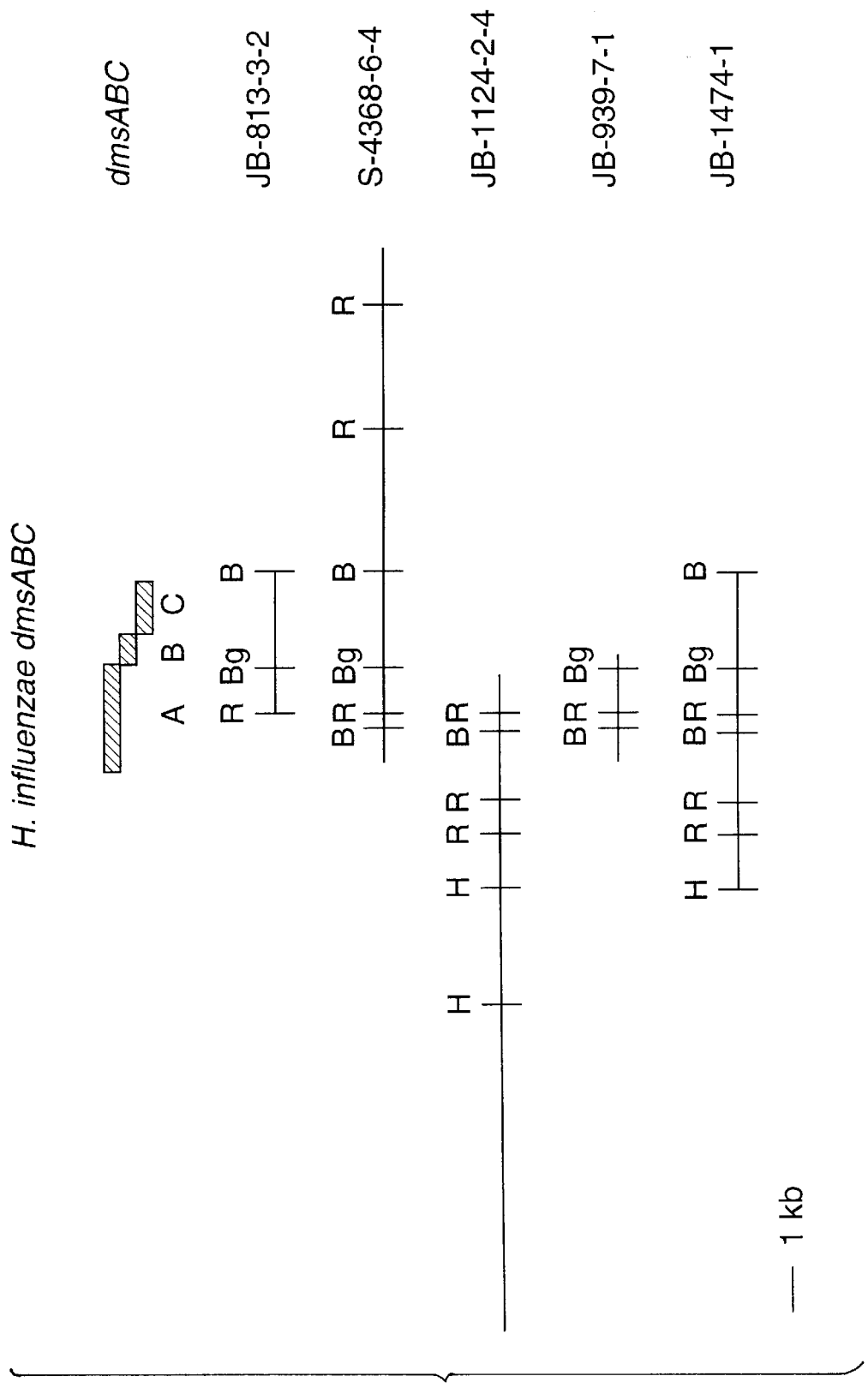
FIG. 1 shows partial restriction maps of the *H. influenzae* clones containing dmsABC. Restriction enzyme sites are B, BamH I; Bg, Bgl II; H, Hind III; R, EcoR I.
Figure 8:
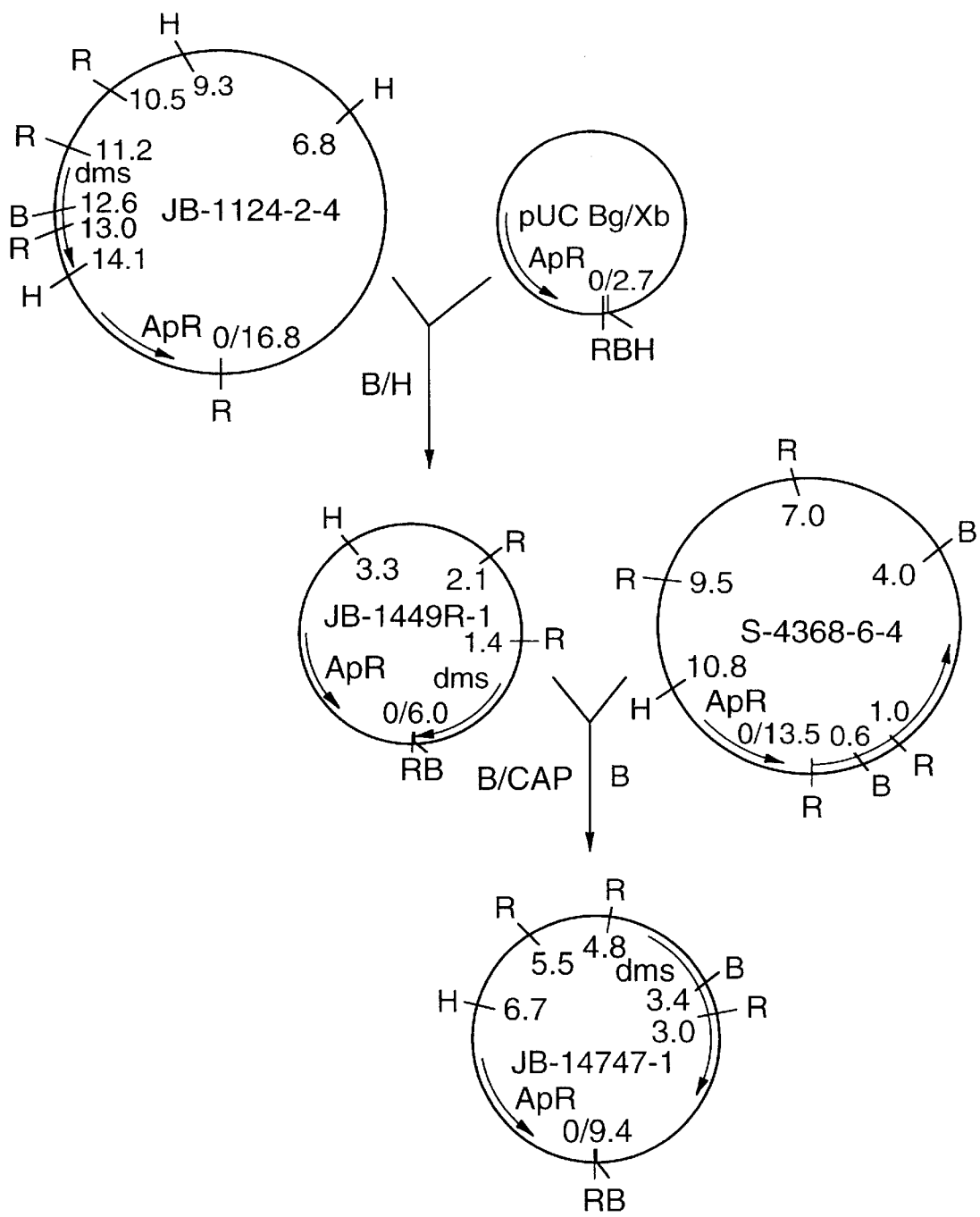
FIG. 8 shows the construction scheme for plasmid JB-1474-1 which contains the complete *H. influenzae* dmsABC operon. Restriction enzyme sites are: B,. BamH I; H, Hind III; R, EcoR I.

*H. influenzae* partial clones JB-813-3-2, S-4368-6-4, JB-1124-2-4 and JB-939-7-1 containing dmsABC fragments were isolated from expression libraries and the partial restriction maps thereof are shown in FIG. 1. Assembly of plasmid JB-1474-1 containing the full-length dmsABC operon from the partial clones is shown in FIG. 8. The complete nucleotide sequence of the dmsABC operon for H. influenzae type b strain Eagan was determined and is shown in FIG. 2 (SEQ ID No: 1). Analysis of the deduced amino acid sequence showed three distinct subunits DmsA (SEQ ID No: 5), DmsB (SEQ ID No: 6) and DmsC (SEQ ID No: 7), each having its individual gene sequence dmsA (SEQ ID No: 2), dmsB (SEQ ID No: 3) and dmsC (SEQ ID No: 4).

A comparative amino acid sequence analysis with the DmsA (SEQ ID No: 8), DmsB (SEQ ID No: 9) and DmsC (SEQ ID No: 10) proteins from *E. coli* was carried out and the extent of homology is shown respectively in FIGS. 3, 4 and 5. In addition, a partial comparative amino acid sequence analysis of the amino acid sequence of the Eagan strain DMS subunits with the derived proteins (SEQ ID Nos: 11 and 12) from the *H. influenzae* non-typable strain SB33 dmsA and dmsB genes showed a high degree of sequence conservation between the two *H. influenzae* strains as seen in FIGS. 6 and 7. There is significant homology between the derived *E. coli* and *H. influenzae* protein sequences. Partial sequence obtained from a NTHi strain SB33 and compared to the *H. influenzae* type b Eagan sequence shows that the two Haemophilus proteins are highly conserved. The discovery of the dimethylsulfoxide reductase enzyme gene in Haemophilus as provided herein provides evidence that *H. influenzae* utilizes a mechanism for survival and growth under anaerobic conditions, similar to that employed by other facultative anaerobes, such as *E. coli*.

The purified and isolated DNA molecules comprising at least a portion coding for a dimethylsulfoxide reductase enzyme or individual subunits thereof of a species of Haemophilus typified by the embodiments described herein are advantageous as:

- nucleic acid probes for the specific identification of Haemophilus strains.
- the products encoded by the DNA molecules are useful as diagnostic reagents, antigens for the production of Haemophilus-specific antisera, for vaccination against the diseases caused by species of Haemophilus and (for example) detecting infection by Haemophilus.
- peptides corresponding to portions of the dimethylsulfoxide reductase enzyme or individual subunits thereof are useful as diagnostic reagents, antigens for the production of Haemophilus-specific antisera, for vaccination against the diseases caused by species of Haemophilus and (for example) for detecting infection by Haemophilus.

The dimethylsulfoxide reductase enzyme and subunits thereof encoded by the nucleic acid molecules of the present invention, and peptides containing sequences corresponding to portions of the dimethylsulfoxide reductase enzyme that are conserved between various isolates of Haemophilus and other bacteria that produce dimethylsulfoxide reductase enzyme, are useful in diagnosis of and immunization against diseases caused by any bacterial strain that produces dimethylsulfoxide reductase enzyme.

The invention extends to nucleic acid molecules encoding a dimethylsulfoxide enzyme of a strain of Haemophilus, or an individual subunit or a fragment or an analog of the dimethylsulfoxide reductase enzyme and a recombinant dimethylsulfoxide reductase enzyme or individual subunit, fragment or analog thereof producible by expression of such nucleic acid molecules for use as an active pharmaceutical substance, particularly as an active ingredient in a vaccine against disease caused by infection with Haemophilus.

It is clearly apparent to one skilled in the art, that the various embodiments of the present invention have many applications in the fields of vaccination, diagnosis, treatment of, for example, Haemophilus infections, and the generation of immunological reagents.

A further non-limiting discussion of such uses is further presented below.

1. Vaccine Preparation and Use

Immunogenic compositions, suitable to be used as vaccines, may be prepared from dimethylsulfoxide reductase enzyme (DMS) and individual subunits thereof as disclosed herein. The vaccine elicits an immune response which produces antibodies, including anti-DMS antibodies and antibodies that are opsonizing or bactericidal. Should the vaccinated subject be challenged by Haemophilus, the antibodies bind to the bacteria and result in its inactivation. Furthermore, opsonizing or bactericidal anti-DMS antibodies may also provide protection by alternative mechanisms. Immunogenic compositions including vaccines may be prepared as injectables, as liquid solutions or emulsions. The DMS, analogs and fragments thereof and/or peptides may be mixed with pharmaceutically acceptable excipients which are compatible with the dimethylsulfoxide reductase enzyme or individual subunits thereof. Such excipients may include, water, saline, dextrose, glycerol, ethanol, and combinations thereof. The immunogenic compositions and vaccines may further contain auxiliary substances such as wetting or emulsifying agents, pH buffering agents, or adjuvants to enhance the effectiveness of the vaccines. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. The immunogenic composition may be provided in combination with a targeting molecule for delivery to specific cells of the immune system or to mucosal surfaces. Some such targeting molecules include vitamin B12 and fragments of bacterial toxins, as described in WO 92/17167 (Biotech Australia Pty. Ltd.), and monoclonal antibodies, as described in U.S. Pat. No. 5,194,254 (Barber et al). Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions take the form of solutions, suspensions, tablets, pills, capsules, sustained release formulations or powders and contain 10–95% of the dimethylsulfoxide reductase or individual fragments thereof, fragment analogs and/or peptides.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize needed, dies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the dimethylsulfoxide reductase enzyme and individual subunits thereof. Suitable regimes for initial administration and booster doses are also variable, but may include an initial administration followed by subsequent administrations. The dosage of the vaccine may also depend on the route of administration and will vary according to the size of the host.

The nucleic acid molecules encoding the dimethylsulfoxide reductase enzyme or individual subunits thereof of the present invention may also be used directly for immunization by administration of the DNA directly, for example by injection for genetic immunization or by constructing a live vector such as Salmonella, BCG, adenovirus, poxvirus, vaccinia or poliovirus. A discussion of some live vectors that have been used to carry heterologous antigens to the immune system are discussed in for example O'Hagan (Ref. 7). Processes for the direct injection of DNA into test subjects for genetic immunization are described in, for example, Ulmer et al. (Ref. 8).

Immunogenicity can be significantly improved if the antigens are co-administered with adjuvants, commonly used as an 0.05 to 1.0 percent solution in phosphate—buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria and mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are emulsified in adjuvants. Many adjuvants are toxic, inducing granulomas, acute and chronic inflammations (Freund's complete adjuvant, FCA), cytolysis (saponins and pluronic polymers) and pyrogenicity, arthritis and anterior uveitis (LPS and MDP). Although FCA is an excellent adjuvant and widely used in research, it is not licensed for use in human or veterinary vaccines because of its toxicity.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (Ref. 9) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. 1990, reported that octadecyl esters of aromatic amino acids complexed with a recombinant hepatitis B surface antigen, enhanced the host immune responses against hepatitis B virus.

2. Immunoassays

The dimethylsulfoxide reductase enzyme or individual subunits thereof of the present invention are useful as immunogens, as antigens in immunoassays including enzyme-linked immunosorbent assays (ELISA), RIAs and other non-enzyme linked antibody binding assays or procedures known in the art for the detection of anti-bacterial, anti-Haemophilus, anti-DMS antibodies. In ELISA assays, the dimethylsulfoxide reductase enzyme or individual subunits thereof are immobilized onto a selected surface, for example a surface capable of binding proteins or peptides such as the wells of a polystyrene microtiter plate. After washing to remove incompletely adsorbed dimethylsulfoxide reductase enzyme or individual subunits thereof, a nonspecific protein such as a solution of bovine serum albumin (BSA) or casein that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample such as clinical or biological materials to be tested in a manner conducive to immune complex (antigen/antibody) formation. This may include diluting the sample with diluents such as BSA, bovine gamma globulin (BGG) and/or phosphate buffered saline (PBS)/Tween. The sample is then allowed to incubate for from 2 to 4 hours, at temperatures such as of the order of 25 to 37° C. Following incubation, the sample-contacted surface is washed to remove non-immunocomplexed material. The washing procedure may include washing with a solution such as PBS/Tween, or a borate buffer.

Following formation of specific immunocomplexes between the test sample and the bound dimethylsulfoxide reductase enzyme and individual subunits thereof and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a color development upon incubating with an appropriate chromogenic substrate. Quantification may then achieved by measuring the degree of color generation using, for example, a visible spectra spectrophotometer.

3. Use of Sequences as Hybridization Probes

The nucleotide sequences of the present invention, comprising the sequence of the dimethylsulfoxide reductase enzyme or individual subunits thereof, now allow for the identification and cloning of the dms genes from any species of Haemophilus.

The nucleic acid molecules comprising the sequence of the dimethylsulfoxide reductase enzyme of the present invention are useful for their ability to selectively form duplex molecules with complementary stretches of other dms genes. Depending on the application, a variety of hybridization conditions may be employed to achieve varying degrees of selectivity of the probe toward the other dms genes. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results. In general, convenient hybridization temperatures in the presence of 50% formamide are: 42° C. for a probe which is 95 to 100% homologous to the target fragment, 37° C. for 90 to 95% homology and 32° C. for 85 to 90% homology.

In a clinical diagnostic embodiment, the nucleic acid sequences of the dms genes of the present invention may be used in combination with an appropriate means, such as a label, for determining hybridization. A wide variety of appropriate indicator means are known in the art, including radioactive, enzymatic, digoxigenin or other ligands, such as avidin/biotin, which are capable of providing a detectable signal. In some diagnostic embodiments, an enzyme tag such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing dms gene sequences.

The nucleic acid sequences of dms genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the dms genes or individual subunits thereof of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label. It is preferred to select nucleic acid sequence portions which are conserved among species of Haemophilus. The selected probe may be at least 18 bp and may be in the range of 30 bp to 90 bp long.

4. Expression of the Dimethylsulfoxide Reductase Enzyme Genes

Plasmid vectors containing replicon and control sequences which are derived from species compatible with the host cell may be used for the expression of the dimethylsulfoxide reductase enzyme genes in expression systems. The vector ordinarily carries a replication site, as well as marking sequences which are capable of providing phenotypic selection in transformed cells. For example, *E. coli* may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. coli* LE392.

Promoters commonly used in recombinant DNA construction include the lactose promoter systems and other promoters such as the T7 promoter system (U.S. Pat. No. 4,952,496). Details concerning the nucleotide sequences of promoters are known, enabling a skilled worker to ligate them functionally with genes. The particular promoter used will generally be a matter of choice depending upon the desired results. Hosts that are appropriate for expression of the dimethylsulfoxide reductase enzyme or individual subunits thereof include E. coli, Bacillus species, Haemophilus, Bordetella, fungi, yeast or the baculovirus expression system may be used.

In accordance with this invention, it is preferred to make the enzyme by recombinant methods, particularly when the naturally occurring dimethylsulfoxide reductase enzyme is purified from a culture of a species of Haemophilus, may include trace amounts of toxic materials or other contaminants. This problem can be avoided by using recombinantly produced DMS proteins in heterologous systems which can be isolated from the host in a manner to minimize contaminants in the purified material. Particularly desirable hosts for expression in this regard may include Gram positive bacteria which do not have LPS and are therefore endotoxin free. Such hosts include species of Bacillus and may be particularly useful for the production of non-pyrogenic dimethylsulfoxide reductase enzyme or individual subunits thereof. Furthermore, recombinant methods of production permit the manufacture of DmsA, DmsB, DmsC individual subunits or fragments thereof separate from one another which is distinct from the normal combined proteins present in Haemophilus.

Biological Deposits

A plasmid JB-1474-1, that contains at least a portion coding for dimethylsulfoxide reductase from Haemophilus influenzae type b Eagan that is described and referred to herein has been deposited with the American Type Culture Collection (ATCC) located at 10801 University Blvd., Manassas. Va. 20110-2209, U.S.A. pursuant to the Budapest Treaty on Jun. 29, 1995 under Designation No. 97,216. Samples of the deposited plasmid will become available to the public upon grant of a patent based upon this United States patent application. The invention described and claimed herein is not to be limited in scope by the plasmid deposited, since the deposited embodiment is intended only as an illustration of the invention. Any equivalent or similar plasmids that encode similar or equivalent antigens as described in this application are within the scope of the invention.

Strains of Haemophilus

Hib strain Eagan is available from Connaught Laboratories Limited, 1755 Steeles Ave. W., Willowdale, Ontario, Canada M2R 3T4.

H. influenzae non-typable strain SB33 was obtained from Dr. Stephen Barenkamp, Department of Pediatrics, School of Medicine, Saint Louis University Medical Centre, St. Louis, Mo. 63104.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry and immunology technology used but not explicitly described in this disclosure and these Examples are amply reported in the scientific literature and are well within the ability of those skilled in the art.

Example 1

This Example illustrates the preparation of chromosomal DNA from H. influenzae strains.

H. influenzae strains were grown on Mueller-Hinton agar or in brain heart infusion broth as described by Harkness et al (Ref. 10).

Cells were pelleted from 50 ml of culture by centrifugation at 5000 rpm for 15–20 minutes, at 4° C. The cell pellet was resuspended in 10 ml of TE (10 mM Tris-HCl, 1 mM EDTA, pH 7.5), pronase and SDS were added to final concentrations of 500 $\mu$g/ml and 1%, respectively. The sample was incubated at 37° C. for 4 hours until a clear lysate was obtained. The lysate was extracted once with Tris-saturated phenol, once with Tris-saturated phenol/chloroform (1:1), and once with chloroform. The final aqueous phase was dialysed for 24 hours against 2×500 ml of 1M NaCl at 4° C., changing the buffer once, and for 24 hours against 2×500 ml of TE at 4° C., changing the buffer once. The final dialysate was aliquotted for use.

Example 2

This Example illustrates the construction of an expression library from H. influenzae type b strain Eagan chromosomal DNA.

Chromosomal DNA was digested with restriction enzymes BamH I and EcoR I, and fragments of 2 to 6 kb in size were purified by gel electrophoresis. Plasmids pEV vrf1, pEV vrf2, and pEV vrf3 (Ref. 11) were digested with restriction enzymes BamH I and EcoR I and ligated with Eagan chromosomal DNA. The ligation mixture was used to transform E. coli strain RRI (pRK248cIts). Cells were grown overnight at 30° C. on YT agar plates containing ampicillin (75 $\mu$g/ml) and tetracycline (15 $\mu$g/ml).

Example 3

This Example illustrates the screening of the expression library with antisera.

Colonies were transferred to nitrocellulose membrane as described by Crowl et al. (Ref. 11) and were grown for 2 hours at 30° C. followed by 2 hours at 42° C. The filters were processed as described by Crowl et al. (Ref. 11) and probed with an antiserum for 2 hours, at ambient temperature, at a 1:100 dilution. The filters were washed, incubated with a 1:100 dilution of $^{125}$I Protein A, washed, and an autoradiogram prepared.

Putative clones were submitted to a second round of screening and several were selected for restriction enzyme analysis and/or sequence analysis. Clones JB-813-3-2, JB-813-3-3, and JB-813-3-5 are found to have identical 3 kb inserts and to encode proteins with homology to E. coli dimethylsulfoxide reductase enzyme.

Example 4

This Example illustrates the construction and screening of a pUC-based Hib strain Eagan library.

Chromosomal DNA from Hib strain Eagan was partially digested with Sau3A I and fragments of 3–10 kb in size were gel purified. Plasmid pUC Bg/Xb is a derivative of pUC8 which has restriction enzyme sites for Bgl II and Xba I in the multiple cloning site. pUC Bg/Xb was digested with BamH I/Bgl II, dephosphorylated, and ligated with isolated DNA fragments. The ligation mixture was used to transform *E. coli* JM109 cells and was selected with ampicillin (75 μg/ml).

Colonies were transferred to nitrocellulose filters and grown several hours at 37° C. Filters were treated with denaturation buffer (1.5M NaCl/0.5M NaOH) for 15 min, neutralization buffer (1.5M NaCl/1.0M, Tris-HCl, pH 7.0) for 2 min, and were washed in 3×SSC for 2 min, before being baked at 80° C. under vacuum for 2 hours, then washed overnight at 65° C. in 3×SSC+0.1% SDS to remove debris. The filters were pre-hybridized at 42° C. for 6 hours, then hybridized overnight at 42° C. in hybridization buffer (50% formamide/20×Denhardt's/5×SSPE/0.1% SDS). The probe was a digoxigenin-labelled EcoR I/BamH I fragment from JB-813-3-2, and the filters were processed for visualization according to the manufacturer's specifications (AMPPD kit, Boehringer Mannheim). Putative clones were submitted to a second round of screening and several were selected for restriction enzyme analysis and/or sequence analysis. Clone S-4368-6-4 was found to contain a 10.8 kb insert encoding part of the dmsA gene, all of the dmsB gene, all of dmsC gene and about 7 kb of 3'-flanking region.

Example 5

This Example illustrates the construction and screening of a pUC-based library containing inserts from non-typable *H. influenzae* (NTHi) strain SB33.

Chromosomal DNA was prepared from NTHi strain SB33 as described above in Example 2 and was partially digested with restriction enzyme Sau3A I. Fragments of 3–10 kb in size were purified by gel electrophoresis. pUC Bg/Xb was digested with BamH I, dephosphorylated, and ligated with the isolated SB33 DNA fragments. The ligation mixture was used to transform *E. coli* JM109 cells. Colonies were processed as above and several putative clones were selected for restriction enzyme analysis and/or sequence analysis. Clones JB-939-7-1 and JB-939-7-5 were found to contain identical 2.3 kb inserts which encoded part of the SB33 DMS A and DMS B proteins.

Example 6

This Example illustrates the screening of an Eagan/EMBL3 library.

*H. influenzae* type b strain Eagan chromosomal DNA was partially digested with Sau3A I and fragments from 5–20 kb in size were ligated with BamH I arms of EMBL3 (Promega). Phage were packaged with the Gigapack II packaging kit and plated onto *E. coli* LE392 cells. Plaques were transferred to nitrocellulose filters and were probed with a digoxigenin-labelled insert from clone JB-939-7-1. Several putative clones were submitted to second round screening and phage DNA was prepared. Inserts were excised using Sal I enzyme and subcloned into pUC Bg/Xb which had been digested with Sal I and dephosphorylated. Clone JB-1124- 2-4 contains a 13.8 kb insert of which ~11.6 kb is 5'-flanking sequence and the remainder encodes part of the Eagan DMS A protein.

Example 7

This Example illustrates the sequencing of the *H. influenzae* dmsA, dmsb and dmsc genes.

Plasmid DNA from clones JB-813-3-2, S-4368-6-4, and JB-1124-2-4 was prepared. Oligonucleotide sequencing primers of 17–25 bp in length were synthesized on an ABI DNA synthesizer and purified by chromatography. Samples were sequenced on an ABI model sequencer using dye terminator chemistry. The nucleotide sequence and derived amino acid sequence of the Eagan dmsABC operon is shown in FIG. 2. A comparison of the derived Eagan DMS A, DMS B, and DMS C amino acid sequences with the *E. coli* proteins is shown in FIGS. 3, 4 and 5.

Plasmid DNA was prepared from clone JB-939-7-1 and sequenced as above. The clone encodes most of DMS A and part of DMS B. The deduced amino acid sequences are compared to the comparable sequences of Hib Eagan DMS in FIGS. 6 and 7.

Example 8

This Example illustrates the construction of plasmid JB-1474-1 which contains the complete *H. influenzae* dmsABC.

None of the clones obtained from the various libraries was full-length, so a single clone containing the complete *H. influenzae* type b strain Eagan dmsABC operon and its flanking regions was constructed (FIG. 8). Plasmid JB-1124-2-4 was digested with Hind III and BamH I to excise a ~3.3 kb insert which contained ~2.5 kb of 5'-flanking sequence and 0.8 kb of dmsA. The fragment was cloned into pUC Bg/Xb which had been digested with BamH I and Hind III, to generate plasmid JB-1449R-1. Plasmid JB-1449R-1 was digested with BamH I and dephosphorylated. Plasmid S-4368-6-4 was digested with BamH I to excise a ~3.4 kb fragment containing ~3 kb of dmsABC and ~0.4 kb of 3'-flanking sequence, which was ligated with the JB-1449R-1 vector fragment. The resulting clone (JB-1474-1) thus contains ~2.5 kb of 5'-flanking region, the complete Hib Eagan dmsABC operon, and ~0.4 kb of 3'-flanking region.

SUMMARY OF THE DISCLOSURE

In summary of this disclosure, the present invention provides purified and isolated DNA molecules containing genes encoding dimethylsulfoxide reductase enzyme and individual subunits thereof from Haemophilus, the sequences of these dms genes and the derived amino acid sequences of the DMS protein subunits. The genes, DNA sequences and recombinant proteins producible by expression of the genes are useful for diagnosis, immunization and the generation of diagnostic and immunological reagents. Modifications are possible within the scope of this invention.

LIST OF REFERENCES

1. Berkowitz et al., (1987) J. Pediatr. 110:509.
2. Claesson et al., (1989) J. Pediatr. 114:97.
3. Black et al., (1991) Pediatr. Infect. Dis. J. 10:97.
4. Bluestone, N. (1982) Engl. J. Med. 306:1399.
5. Bilous and Weiner (1988) J. Bacteriol. 170:1511–1518
6. Bilous et al., (1988) Molec. Microbiol. 2:785–795
7. O'Hagan (1992) Clin Pharmokinet. 22:1.
8. Ulmer et al., (1993) Curr. Opinion Invest. Drugs. 2 (9): 983–989.
9. Lockhoff et al., (1991) Chem. Int. Ed. Engl. 30:1611.
10. Harkness et al., (1992) J. Bacteriol. 174:2425.
11. Crowl et al., (1985) Gene 38:31–38

What we claim is:

1. A purified and isolated nucleic acid molecule encoding a dimethylsulfoxide reductase enzyme of a strain of Haemophilus or an individual subunit thereof or an enzymatically-active fragment of the dimethylsulfoxide reductase enzyme.

2. The nucleic acid molecule of claim 1 encoding only an individual subunit of the dimethylsulfoxide reductase enzyme.

3. The nucleic acid molecule of claim 2 wherein said subunit is subunit A, B or C.

4. A purified and isolated nucleic acid molecule encoding a dimethylsulfoxide reductase enzyme of a strain of Haemophilus or an individual subunit thereof having a DNA sequence selected from the group consisting of:
   (a) any one of the DNA sequences set out in FIG. 2 (SEQ ID Nos. 1, 2, 3 or 4) or a complementary DNA sequence thereto;
   (b) a DNA sequence encoding one of the amino acid sequences set out in FIGS. 2, 6 or 7 (SEQ ID Nos. 5, 6, 7, 11 and 12) or a complementary DNA sequence thereto; and
   (c) a DNA sequence having at least about 90% of sequence identity to any one of the DNA sequences defined in (a) or (b).

5. A vector adapted for transformation of a host comprising the nucleic acid molecule of claim 1 or 4, and expression means operatively coupled to the nucleic acid molecule for expression by the host of said dimethylsulfoxide reductase enzyme of a strain of Haemophilus or the individual subunit thereof, or the enzymatically-active fragment of the dimethylsulfoxide reductase enzyme.

6. A vector which is plasmid JB-1474-1 having ATCC Designation No. 97216.

7. A host transformed by the expression vector of claim 5.

8. An immunogenic composition, comprising at least one active component selected from the group consisting of:
   (A) a purified and isolated nucleic acid molecule encoding a dimethylsulfoxide reductase enzyme of a strain of Haemophilus or an individual subunit thereof or an enzymatically-active fragment of the dimethylsulfoxide reductase; and
   (B) a purified and isolated nucleic acid molecule having a DNA sequence selected from the group consisting of:
      (a) any one of the DNA sequences set out in FIG. 2 (SEQ ID Nos: 1, 2, 3 and 4) or a complementary DNA sequence thereto;
      (b) a DNA sequence encoding one of the amino acid sequences set out in FIGS. 2, 6 or 7 (SEQ ID Nos: 5, 6, 7, 11 and 12) or a complementary DNA sequence thereto; and
      (c) a DNA sequence having at least about 90% sequence identity to any one of the DNA sequences defined in (a) or (b);

and a pharmaceutically acceptable carrier therefor, said at least one active component producing an immune response when administered to a host.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 4051 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: join(65..2482, 2496..3110, 3115..3951)

(xi) SEQUENCE DESCRIPTION: SEQ ID NO:1:

```
TATACAAAGA TTATAATTAA CTCGTTTTAG TTATTTTTCA ATCTGACTGT GGGGGAACGA        60

TATA ATG AGT AAC TTT AAT CAA ATA AGT CGC CGA GAT TTT GTC AAG GCG        109
     Met Ser Asn Phe Asn Gln Ile Ser Arg Arg Asp Phe Val Lys Ala
      1               5                  10                  15

TCA TCT GCG GGA GCT GCA CTG GCA GTT TCA AAT CTT ACT TTA CCT TTC        157
Ser Ser Ala Gly Ala Ala Leu Ala Val Ser Asn Leu Thr Leu Pro Phe
                 20                  25                  30

AAT GTA ATG GCT AAA GAG ACA CAA CGC CTC AAT GAA AAT AAT CAA GAA        205
Asn Val Met Ala Lys Glu Thr Gln Arg Leu Asn Glu Asn Asn Gln Glu
             35                  40                  45

CGT ATT GTT TGG AGT GCT TGT ACA GTA AAC TGT GGT AGC CGT TGT CCA        253
Arg Ile Val Trp Ser Ala Cys Thr Val Asn Cys Gly Ser Arg Cys Pro
         50                  55                  60

TTA CGA ATG CAC GTA AAA GAT AAC CGA ATC ACT TAT GTG GAA ACC GAT        301
Leu Arg Met His Val Lys Asp Asn Arg Ile Thr Tyr Val Glu Thr Asp
     65                  70                  75

AAT ACG GGG ACA GAA ACA TAT AAT CTT GAT CAT CAG GTT CGT GCT TGT        349
Asn Thr Gly Thr Glu Thr Tyr Asn Leu Asp His Gln Val Arg Ala Cys
 80                  85                  90                  95

CTA CGT GGA CGT TCT ATG CGT CGT CGA GTG TAT AAC CCA GAC CGC TTA        397
Leu Arg Gly Arg Ser Met Arg Arg Arg Val Tyr Asn Pro Asp Arg Leu
                100                 105                 110

AAA TAT CCA ATG AAA CGT ATA GGT AAA CGC GGA GAA GGT AAA TTC AAA        445
Lys Tyr Pro Met Lys Arg Ile Gly Lys Arg Gly Glu Gly Lys Phe Lys
            115                 120                 125

CGA ATC AGT TGG GAT GAG GCT TTA ACT GAA ATT GCA TAC GCA TTG AAA        493
Arg Ile Ser Trp Asp Glu Ala Leu Thr Glu Ile Ala Tyr Ala Leu Lys
        130                 135                 140

CGC AAT ATC AAA AAA TAT GGC AAT GAA TCA ATT TAT TTA AAC TAT GGT        541
Arg Asn Ile Lys Lys Tyr Gly Asn Glu Ser Ile Tyr Leu Asn Tyr Gly
    145                 150                 155

ACG GGA ACA CTC GGT GGC ACA ATG GCT AAA TCT TGG CCA CCT GCA TCC        589
Thr Gly Thr Leu Gly Gly Thr Met Ala Lys Ser Trp Pro Pro Ala Ser
160                 165                 170                 175

ACT ATG ATC GCT CGT TTT ATG AAT TGT ATT GGT GGA TAT TTA AAC CAT        637
Thr Met Ile Ala Arg Phe Met Asn Cys Ile Gly Gly Tyr Leu Asn His
                180                 185                 190

TAT GGT GAT TAC AGC ACC GCA CAA ATT GCA GTC GGT TTA GAT TAT ACC        685
Tyr Gly Asp Tyr Ser Thr Ala Gln Ile Ala Val Gly Leu Asp Tyr Thr
            195                 200                 205

TAT GGT GGT GGT TGG GCA TTG GGA AAT GGA ATG GCT GAC ATT GAA AAC        733
Tyr Gly Gly Gly Trp Ala Leu Gly Asn Gly Met Ala Asp Ile Glu Asn
        210                 215                 220
```

-continued

| | |
|---|---|
| ACC AAA TTA ATA GTG TTA TTC GGT AAT AAT CCT GCA GAA ACT CGT ATG<br>Thr Lys Leu Ile Val Leu Phe Gly Asn Asn Pro Ala Glu Thr Arg Met<br>     225                      230                    235 | 781 |
| AGT GGA GGT GGT TTA ACT TAT TGT ATT GAA CAA GCC AAA GCT CGT TCC<br>Ser Gly Gly Gly Leu Thr Tyr Cys Ile Glu Gln Ala Lys Ala Arg Ser<br>240                      245                    250                    255 | 829 |
| AAT GCC AAA ATG ATT ATT ATC GAT CCT CGT TAT AAT GAT ACT GGT GCA<br>Asn Ala Lys Met Ile Ile Ile Asp Pro Arg Tyr Asn Asp Thr Gly Ala<br>                    260                    265                    270 | 877 |
| GGG CGT GAA GAT GAG TGG ATC CCA ATT CGT CCG GGG ACT GAT GCA GCC<br>Gly Arg Glu Asp Glu Trp Ile Pro Ile Arg Pro Gly Thr Asp Ala Ala<br>              275                    280                    285 | 925 |
| CTT GTT GCT GCC CTT GCT TAT GTA ATG ATT CAA GAA AAT CTC GTG GAT<br>Leu Val Ala Ala Leu Ala Tyr Val Met Ile Gln Glu Asn Leu Val Asp<br>          290                    295                    300 | 973 |
| CAA CCT TTC TTA GAT AAA TAT TGT GTT GGT TAT GAT GAA AAA ACA TTA<br>Gln Pro Phe Leu Asp Lys Tyr Cys Val Gly Tyr Asp Glu Lys Thr Leu<br>          305                    310                    315 | 1021 |
| CCT GCG GAT GCC CCT AAA AAT GGT CAT TAT AAA GCC TAT ATT TTA GGT<br>Pro Ala Asp Ala Pro Lys Asn Gly His Tyr Lys Ala Tyr Ile Leu Gly<br>320                      325                    330                    335 | 1069 |
| TAT GGT AAT GAT GGT ATC GCT AAA ACT CCA GAA TGG GCG GCT AAA ATC<br>Tyr Gly Asn Asp Gly Ile Ala Lys Thr Pro Glu Trp Ala Ala Lys Ile<br>                    340                    345                    350 | 1117 |
| ACG GGT ATT CCG GCG GAG AGA ATT ATT AAA CTC GCA CGT GAA ATT GGC<br>Thr Gly Ile Pro Ala Glu Arg Ile Ile Lys Leu Ala Arg Glu Ile Gly<br>              355                    360                    365 | 1165 |
| AGC ACA AAA CCT GCC TTT ATT TCC CAA GGT TGG GGG CCT CAA CGT CGT<br>Ser Thr Lys Pro Ala Phe Ile Ser Gln Gly Trp Gly Pro Gln Arg Arg<br>          370                    375                    380 | 1213 |
| AGT AAT GGA GAA TTA ATC TCT CGT GCC ATT GCG ATG TTG CCA ATC TTA<br>Ser Asn Gly Glu Leu Ile Ser Arg Ala Ile Ala Met Leu Pro Ile Leu<br>385                      390                    395 | 1261 |
| ACA GGT AAT GTT GGA ATT CAC GGC GGT AAC ACT GGT GCA CGT GAA AGT<br>Thr Gly Asn Val Gly Ile His Gly Gly Asn Thr Gly Ala Arg Glu Ser<br>400                      405                    410                    415 | 1309 |
| GCG TAT AGC ATT CCA TTT GTG CGG ATG CCA ACG CTA AAA AAT CCT ATG<br>Ala Tyr Ser Ile Pro Phe Val Arg Met Pro Thr Leu Lys Asn Pro Met<br>                    420                    425                    430 | 1357 |
| AAA GCA AGC ATT CCA ATG TTT TTA GGG ACA GAT GCA ATT ATT CGT GGC<br>Lys Ala Ser Ile Pro Met Phe Leu Gly Thr Asp Ala Ile Ile Arg Gly<br>              435                    440                    445 | 1405 |
| ACA GAA ATG ACC GCA CTT ACA GAT GGT ATT CGT GGT GTT GAT AAA TTA<br>Thr Glu Met Thr Ala Leu Thr Asp Gly Ile Arg Gly Val Asp Lys Leu<br>          450                    455                    460 | 1453 |
| TCG CCC CCA ATT AAA GTA ATT TGG AAT TAC GCA AGT AAC TGT TTG ATT<br>Ser Pro Pro Ile Lys Val Ile Trp Asn Tyr Ala Ser Asn Cys Leu Ile<br>465                      470                    475 | 1501 |
| AAT CAA CAC GCA CAA ATC AAT CGT ACT CAC GAT ATT TTA CAA GAT GAT<br>Asn Gln His Ala Gln Ile Asn Arg Thr His Asp Ile Leu Gln Asp Asp<br>480                      485                    490                    495 | 1549 |
| ACG CAA TGT GAA ATG ATC ATT ACT ATT GAT AAT CAT ATG ACA TCT ACT<br>Thr Gln Cys Glu Met Ile Ile Thr Ile Asp Asn His Met Thr Ser Thr<br>                    500                    505                    510 | 1597 |
| GCC AAA TAC AGT GAT ATT TTA TTA CCA GAT TGT CCA ACT TCA GAA CAA<br>Ala Lys Tyr Ser Asp Ile Leu Leu Pro Asp Cys Pro Thr Ser Glu Gln<br>              515                    520                    525 | 1645 |
| ATG GAT TTC GCT TTA GAT GCC TTT GTA TCC AAT ATG GCA TAT GTC ATT<br>Met Asp Phe Ala Leu Asp Ala Phe Val Ser Asn Met Ala Tyr Val Ile | 1693 |

-continued

```
             530                     535                     540
TTT GCA GAT CAA GTG ATC AAA CCA TCT TTT GAA TGT AGA CCT ATT TAC    1741
Phe Ala Asp Gln Val Ile Lys Pro Ser Phe Glu Cys Arg Pro Ile Tyr
    545                     550                     555

GAT ATG TTA AGT GAT TTA GCT GAG AAA ATG GGC GTA AAA GAA AAA TTT    1789
Asp Met Leu Ser Asp Leu Ala Glu Lys Met Gly Val Lys Glu Lys Phe
560                     565                     570                 575

ACT GAA GGA AGA ACA CAA GAA GAA TGG TTA CGC CAT ATT TAT GAG CAA    1837
Thr Glu Gly Arg Thr Gln Glu Glu Trp Leu Arg His Ile Tyr Glu Gln
                        580                     585                     590

TCT CGA GAA AAA TTA CCT GAA TTA CCT ACT TTT GAA GAA TTT AGA CAA    1885
Ser Arg Glu Lys Leu Pro Glu Leu Pro Thr Phe Glu Glu Phe Arg Gln
                595                     600                     605

CAA GGT ATT TTT AAA AAA GTT GAT CCT AAT GGC TTT AAA GTT GCA TAC    1933
Gln Gly Ile Phe Lys Lys Val Asp Pro Asn Gly Phe Lys Val Ala Tyr
            610                     615                     620

AAA GAT TTC CGT GAT AAT CCA GAA GCC CAT CCA CTT AAA ACG CCA TCT    1981
Lys Asp Phe Arg Asp Asn Pro Glu Ala His Pro Leu Lys Thr Pro Ser
        625                     630                     635

GGC AAA ATT GAA ATT TAT TCT TCT CGT CTA GCT GAA ATA GCA AAA ACT    2029
Gly Lys Ile Glu Ile Tyr Ser Ser Arg Leu Ala Glu Ile Ala Lys Thr
640                     645                     650                     655

TGG AAA TTA GCA GAA GAT GAC GTA ATT CAT CCC TTA CCT ATT CAC GCC    2077
Trp Lys Leu Ala Glu Asp Asp Val Ile His Pro Leu Pro Ile His Ala
                        660                     665                     670

CAA AGT TTT GAG CAT TAC GGT GAT CCA TTA ATG GAA AAA TAT CCG TTA    2125
Gln Ser Phe Glu His Tyr Gly Asp Pro Leu Met Glu Lys Tyr Pro Leu
                675                     680                     685

CAA CTA AGT GGT TTT CAC TAT AAA GCG AGA ACC CAT TCA ACT TAT GGC    2173
Gln Leu Ser Gly Phe His Tyr Lys Ala Arg Thr His Ser Thr Tyr Gly
            690                     695                     700

AAT GTG GAT GTA TTA AAA GCA GCT AAT CCA CAA GAA GTT TGG ATG AAT    2221
Asn Val Asp Val Leu Lys Ala Ala Asn Pro Gln Glu Val Trp Met Asn
        705                     710                     715

CCT ATT GAT GCA AAA CCT CGT AAT ATT AAA AAT GGC GAT ATG ATT CGT    2269
Pro Ile Asp Ala Lys Pro Arg Asn Ile Lys Asn Gly Asp Met Ile Arg
720                     725                     730                     735

ATC TTT AAT GAT CGA GGC GAA GTA CAT ATT AAT GTA AAA ATT ACA CCC    2317
Ile Phe Asn Asp Arg Gly Glu Val His Ile Asn Val Lys Ile Thr Pro
                        740                     745                     750

CGT ATT ATT CCA GGG GTT GTG GCA TTA AGC GAG GGG GCT TGG TAT GCA    2365
Arg Ile Ile Pro Gly Val Val Ala Leu Ser Glu Gly Ala Trp Tyr Ala
                755                     760                     765

CCA GAT AAA GAT CGT ATC GAT CAT TCA GGT TGC ATT AAT GTA CTT ACG    2413
Pro Asp Lys Asp Arg Ile Asp His Ser Gly Cys Ile Asn Val Leu Thr
            770                     775                     780

ACA CAA CGC CCA TCA CCG CTT GCG AAA GGT AAT CCG CAA CAT TCT AAT    2461
Thr Gln Arg Pro Ser Pro Leu Ala Lys Gly Asn Pro Gln His Ser Asn
        785                     790                     795

TTA GTT CAA GTG GAA CGT TTG TAGGGGGATA ATT ATG GAA CAA TAT GGT     2510
Leu Val Gln Val Glu Arg Leu                 Met Glu Gln Tyr Gly
800                     805                                         810

TTT TAT TTT GAT TCT GAA CGT TGC ACA GGC TGT AAA ACT TGT GAA TTA    2558
Phe Tyr Phe Asp Ser Glu Arg Cys Thr Gly Cys Lys Thr Cys Glu Leu
                815                     820                     825

GCC TGT AAG GAT TAC AAA GAT CTT GGC ACA GAA GTC AAT TTT CGT CGT    2606
Ala Cys Lys Asp Tyr Lys Asp Leu Gly Thr Glu Val Asn Phe Arg Arg
            830                     835                     840

ATT TAT GAA TAT ACA GGT GGT CAG TGG AAT CAA CAA GCA GAT GGA TGC    2654
```

```
Ile Tyr Glu Tyr Thr Gly Gly Gln Trp Asn Gln Gln Ala Asp Gly Cys
    845                 850                 855

TGG CAT CAA AAT ATA TTT GGT TAT TAT ATG TCT ATT TCT TGT AAT CAT          2702
Trp His Gln Asn Ile Phe Gly Tyr Tyr Met Ser Ile Ser Cys Asn His
860                 865                 870                 875

TGT GCA GAT CCT GCT TGT ACA AAA GTT TGC CCA ACT GGT GCA ATG CAC          2750
Cys Ala Asp Pro Ala Cys Thr Lys Val Cys Pro Thr Gly Ala Met His
                880                 885                 890

AAA AAT GCA GAT GGT TTC GTG ATC GTC AAT GAA GAA ATT TGT ATC GGT          2798
Lys Asn Ala Asp Gly Phe Val Ile Val Asn Glu Glu Ile Cys Ile Gly
            895                 900                 905

TGT CGT TAT TGT CAT ATG GCG TGT CCT TAT GAT GCA CCG CAA TAT GAT          2846
Cys Arg Tyr Cys His Met Ala Cys Pro Tyr Asp Ala Pro Gln Tyr Asp
        910                 915                 920

GCA CAA AAA GGT CAT ATG ACA AAA TGT GAT GGA TGT TAT TCT CGC GTA          2894
Ala Gln Lys Gly His Met Thr Lys Cys Asp Gly Cys Tyr Ser Arg Val
    925                 930                 935

AAA TCA GGT CAA AAA CCG ATT TGT GTT GAT GCC TGC CCA CTA CGA GCA          2942
Lys Ser Gly Gln Lys Pro Ile Cys Val Asp Ala Cys Pro Leu Arg Ala
940                 945                 950                 955

TTG GAT TTC GCT CCT ATT GAT GAA CTT CGA ACA AAA TAT GGC ACA CAA          2990
Leu Asp Phe Ala Pro Ile Asp Glu Leu Arg Thr Lys Tyr Gly Thr Gln
                960                 965                 970

GCC TCC ATC GCA CCA CTA CCA CCG ACT GAT ATC ACT CAA CCA AAT TTA          3038
Ala Ser Ile Ala Pro Leu Pro Pro Thr Asp Ile Thr Gln Pro Asn Leu
            975                 980                 985

GTG GTA AAA CCC AAT AAA TAC GCT CGT TTA AGT GGC GAT ACA AGT GGG          3086
Val Val Lys Pro Asn Lys Tyr Ala Arg Leu Ser Gly Asp Thr Ser Gly
        990                 995                 1000

TTC TTA GGA AAC CCA AGA GAG GTG TAAG ATG AAT ACA GGA TTA TAT GAA         3135
Phe Leu Gly Asn Pro Arg Glu Val     Met Asn Thr Gly Leu Tyr Glu
    1005                1010              1015

CTG CCA TTA GTA TTT TTT ACA GTT TTG GCA CAA AGT GCG GCC GGT GCT          3183
Leu Pro Leu Val Phe Phe Thr Val Leu Ala Gln Ser Ala Ala Gly Ala
    1020                1025                1030

TGG CTT GTT TTC ACA TTT GTA CTA TTA AAT GAG AAA AAT ACA AAA AGT          3231
Trp Leu Val Phe Thr Phe Val Leu Leu Asn Glu Lys Asn Thr Lys Ser
1035                1040                1045                1050

CGC ACT TAT ATT CAT AAA GTA ATG TTT GTG ATT TTG GCT TTA CTA GGT          3279
Arg Thr Tyr Ile His Lys Val Met Phe Val Ile Leu Ala Leu Leu Gly
                1055                1060                1065

ATT GGA TTT ATT GCT TCC ATT ATG CAT CTT GGC TTA CCT ATA CGT GCA          3327
Ile Gly Phe Ile Ala Ser Ile Met His Leu Gly Leu Pro Ile Arg Ala
            1070                1075                1080

TTT AAT TCA CTT AAT CGA GTC GGC TCA TCA ATG ATG AGT AAT GAA ATT          3375
Phe Asn Ser Leu Asn Arg Val Gly Ser Ser Met Met Ser Asn Glu Ile
        1085                1090                1095

GCC GCT GGT GCA ATA TTT TTC ACA TTA GCA GGT TTC TAC TGG CTG ATT          3423
Ala Ala Gly Ala Ile Phe Phe Thr Leu Ala Gly Phe Tyr Trp Leu Ile
    1100                1105                1110

GCA ATT TTA GGT AAA ATG CCA GTT TCA CTT GGA AAT GTA TGG CGA ATT          3471
Ala Ile Leu Gly Lys Met Pro Val Ser Leu Gly Asn Val Trp Arg Ile
1115                1120                1125                1130

GTG ACC GCC CTT ATC GGC ATA CTA TTT ATG TAT GTA ATG AAT CAG GTT          3519
Val Thr Ala Leu Ile Gly Ile Leu Phe Met Tyr Val Met Asn Gln Val
                1135                1140                1145

TAC CAT ATT ACA AGC ATA CCA ACT TGG AAT AAT GCA TTA ACC TCT TGG          3567
Tyr His Ile Thr Ser Ile Pro Thr Trp Asn Asn Ala Leu Thr Ser Trp
            1150                1155                1160
```

```
TCA TTC TAC CTT ACC GTT GTA TTA GGT GGA TTA ACA TTG AGC TAT GCG      3615
Ser Phe Tyr Leu Thr Val Val Leu Gly Gly Leu Thr Leu Ser Tyr Ala
        1165                1170                1175

TTA TTA ATC CCT AAT AAA CAA CGT GAA TAT CAG CTT CAG CAT CTG CCA      3663
Leu Leu Ile Pro Asn Lys Gln Arg Glu Tyr Gln Leu Gln His Leu Pro
1180                1185                1190

AGT TTA TTC GCC ATT GGG GTA TCA TTG GTC GCA ATA GTA GCC ATA TAT      3711
Ser Leu Phe Ala Ile Gly Val Ser Leu Val Ala Ile Val Ala Ile Tyr
1195                1200                1205                1210

CAA GGC TTC AAT TTA CAC AAT ATT CAC AGT GCT ATT CAA AAT GCC GCT      3759
Gln Gly Phe Asn Leu His Asn Ile His Ser Ala Ile Gln Asn Ala Ala
            1215                1220                1225

GAC CTC GTA CCA AAT TAT GCC ATA ATG ACC GTA ACT CGC TTA TGT TTA      3807
Asp Leu Val Pro Asn Tyr Ala Ile Met Thr Val Thr Arg Leu Cys Leu
        1230                1235                1240

CTT TCC ATT GTA GCT TTC CTC TTA TTC CGA GTG AAA AAC ATA GGA CTA      3855
Leu Ser Ile Val Ala Phe Leu Leu Phe Arg Val Lys Asn Ile Gly Leu
            1245                1250                1255

TTA GGT ATT TCC GTT CTA TTA ACG TTA GTA GCT GAA GGC ATC GGC CGC      3903
Leu Gly Ile Ser Val Leu Leu Thr Leu Val Ala Glu Gly Ile Gly Arg
        1260                1265                1270

GTA TTA TTT TAT GGA TTA CAT ATG ACT TAC GGC ATG GCG ATT GGT GGT      3951
Val Leu Phe Tyr Gly Leu His Met Thr Tyr Gly Met Ala Ile Gly Gly
1275                1280                1285                1290

TAAATTATGT TGAGGCGTAT TGCATACGCC TCAATTTTTA GAAACGTTAA TTAGTAATAT    4011

TTAACCACCC CTCATATCCC CATTCACTAA TGACAATTGG                          4051

(2) INFORMATION FOR SEQ ID NO:2:

(i) SEQUENCE CHARACTERISTICS:
        (A) LENGTH: 2418 base pairs
        (B) TYPE: nucleic acid
        (C) STRANDEDNESS: single
        (D) TOPOLOGY: linear (xi) SEQUENCE DESCRIPTION: SEQ ID NO:2:

ATGAGTAACT TTAATCAAAT AAGTCGCCGA GATTTTGTCA AGGCGTCATC TGCGGGAGCT     60

GCACTGGCAG TTTCAAATCT TACTTTACCT TTCAATGTAA TGGCTAAAGA GACACAACGC    120

CTCAATGAAA ATAATCAAGA ACGTATTGTT TGGAGTGCTT GTACAGTAAA CTGTGGTAGC    180

CGTTGTCCAT TACGAATGCA CGTAAAAGAT AACCGAATCA CTTATGTGGA AACCGATAAT    240

ACGGGGACAG AAACATATAA TCTTGATCAT CAGGTTCGTG CTTGTCTACG TGGACGTTCT    300

ATGCGTCGTC GAGTGTATAA CCCAGACCGC TTAAAATATC CAATGAAACG TATAGGTAAA    360

CGCGGAGAAG GTAAATTCAA ACGAATCAGT TGGGATGAGG CTTTAACTGA AATTGCATAC    420

GCATTGAAAC GCAATATCAA AAAATATGGC AATGAATCAA TTTATTTAAA CTATGGTACG    480

GGAACACTCG GTGGCACAAT GGCTAAATCT TGGCCACCTG CATCCACTAT GATCGCTCGT    540

TTTATGAATT GTATTGGTGG ATATTTAAAC CATTATGGTG ATTACAGCAC CGCACAAATT    600

GCAGTCGGTT TAGATTATAC CTATGGTGGT GGTTGGGCAT TGGGAAATGG AATGGCTGAC    660

ATTGAAAACA CCAAATTAAT AGTGTTATTC GGTAATAATC CTGCAGAAAC TCGTATGAGT    720

GGAGGTGGTT TAACTTATTG TATTGAACAA GCCAAAGCTC GTTCCAATGC CAAAATGATT    780

ATTATCGATC CTCGTTATAA TGATACTGGT GCAGGGCGTG AAGATGAGTG GATCCCAATT    840

CGTCCGGGGA CTGATGCAGC CCTTGTTGCT GCCCTTGCTT ATGTAATGAT TCAAGAAAAT    900

CTCGTGGATC AACCTTTCTT AGATAAATAT TGTGTTGGTT ATGATGAAAA AACATTACCT    960
```

-continued

```
GCGGATGCCC CTAAAAATGG TCATTATAAA GCCTATATTT TAGGTTATGG TAATGATGGT      1020

ATCGCTAAAA CTCCAGAATG GGCGGCTAAA ATCACGGGTA TTCCGGCGGA GAGAATTATT      1080

AAACTCGCAC GTGAAATTGG CAGCACAAAA CCTGCCTTTA TTTCCCAAGG TTGGGGGCCT      1140

CAACGTCGTA GTAATGGAGA ATTAATCTCT CGTGCCATTG CGATGTTGCC AATCTTAACA      1200

GGTAATGTTG GAATTCACGG CGGTAACACT GGTGCACGTG AAAGTGCGTA TAGCATTCCA      1260

TTTGTGCGGA TGCCAACGCT AAAAAATCCT ATGAAAGCAA GCATTCCAAT GTTTTTAGGG      1320

ACAGATGCAA TTATTCGTGG CACAGAAATG ACCGCACTTA CAGATGGTAT TCGTGGTGTT      1380

GATAAATTAT CGCCCCCAAT TAAAGTAATT TGGAATTACG CAAGTAACTG TTTGATTAAT      1440

CAACACGCAC AAATCAATCG TACTCACGAT ATTTTACAAG ATGATACGCA ATGTGAAATG      1500

ATCATTACTA TTGATAATCA TATGACATCT ACTGCCAAAT ACAGTGATAT TTTATTACCA      1560

GATTGTCCAA CTTCAGAACA AATGGATTTC GCTTTAGATG CCTTTGTATC CAATATGGCA      1620

TATGTCATTT TTGCAGATCA AGTGATCAAA CCATCTTTTG AATGTAGACC TATTTACGAT      1680

ATGTTAAGTG ATTTAGCTGA GAAAATGGGC GTAAAAGAAA AATTTACTGA AGGAAGAACA      1740

CAAGAAGAAT GGTTACGCCA TATTTATGAG CAATCTCGAG AAAAATTACC TGAATTACCT      1800

ACTTTTGAAG AATTTAGACA ACAAGGTATT TTTAAAAAAG TTGATCCTAA TGGCTTTAAA      1860

GTTGCATACA AAGATTTCCG TGATAATCCA GAAGCCCATC CACTTAAAAC GCCATCTGGC      1920

AAAATTGAAA TTTATTCTTC TCGTCTAGCT GAAATAGCAA AAACTTGGAA ATTAGCAGAA      1980

GATGACGTAA TTCATCCCTT ACCTATTCAC GCCCAAAGTT TGAGCATTA CGGTGATCCA       2040

TTAATGAAAA AATATCCGTT ACAACTAAGT GGTTTTCACT ATAAAGCGAG AACCCATTCA      2100

ACTTATGGCA ATGTGGATGT ATTAAAAGCA GCTAATCCAC AAGAAGTTTG GATGAATCCT      2160

ATTGATGCAA AACCTCGTAA TATTAAAAAT GGCGATATGA TTCGTATCTT TAATGATCGA      2220

GGCGAAGTAC ATATTAATGT AAAAATTACA CCCCGTATTA TTCCAGGGGT TGTGGCATTA      2280

AGCGAGGGGG CTTGGTATGC ACCAGATAAA GATCGTATCG ATCATTCAGG TTGCATTAAT      2340

GTACTTACGA CACAACGCCC ATCACCGCTT GCGAAAGGTA ATCCGCAACA TTCTAATTTA      2400

GTTCAAGTGG AACGTTTG                                                   2418
```

(2) INFORMATION FOR SEQ ID NO:3:

(i) SEQUENCE CHARACTERISTICS:
        (A) LENGTH: 615 base pairs
        (B) TYPE: nucleic acid
        (C) STRANDEDNESS: single
        (D) TOPOLOGY: linear (xi) SEQUENCE DESCRIPTION: SEQ ID NO:3:

```
ATGGAACAAT ATGGTTTTTA TTTTGATTCT GAACGTTGCA CAGGCTGTAA AACTTGTGAA        60

TTAGCCTGTA AGGATTACAA AGATCTTGGC ACAGAAGTCA ATTTTCGTCG TATTTATGAA       120

TATACAGGTG GTCAGTGGAA TCAACAAGCA GATGGATGCT GGCATCAAAA TATATTTGGT       180

TATTATATGT CTATTTCTTG TAATCATTGT GCAGATCCTG CTTGTACAAA AGTTTGCCCA       240

ACTGGTGCAA TGCACAAAAA TGCAGATGGT TTCGTGATCG TCAATGAAGA AATTTGTATC       300

GGTTGTCGTT ATTGTCATAT GGCGTGTCCT TATGATGCAC CGCAATATGA TGCACAAAAA       360

GGTCATATGA CAAAATGTGA TGGATGTTAT TCTCGCGTAA AATCAGGTCA AAAACCGATT       420

TGTGTTGATG CCTGCCCACT ACGAGCATTG GATTTCGCTC CTATTGATGA ACTTCGAACA       480

AAATATGGCA CACAAGCCTC CATCGCACCA CTACCACCGA CTGATATCAC TCAACCAAAT       540
```

-continued

```
TTAGTGGTAA AACCCAATAA ATACGCTCGT TTAAGTGGCG ATACAAGTGG GTTCTTAGGA      600

AACCCAAGAG AGGTG                                                       615
```

(2) INFORMATION FOR SEQ ID NO:4:

(i) SEQUENCE CHARACTERISTICS:
        (A) LENGTH: 837 base pairs
        (B) TYPE: nucleic acid
        (C) STRANDEDNESS: single
        (D) TOPOLOGY: linear (xi) SEQUENCE DESCRIPTION: SEQ ID NO:4:

```
ATGAATACAG GATTATATGA ACTGCCATTA GTATTTTTTA CAGTTTTGGC ACAAAGTGCG       60

GCCGGTGCTT GGCTTGTTTT CACATTTGTA CTATTAAATG AGAAAAATAC AAAAAGTCGC      120

ACTTATATTC ATAAAGTAAT GTTTGTGATT TTGGCTTTAC TAGGTATTGG ATTTATTGCT      180

TCCATTATGC ATCTTGGCTT ACCTATACGT GCATTTAATT CACTTAATCG AGTCGGCTCA      240

TCAATGATGA GTAATGAAAT TGCCGCTGGT GCAATATTTT TCACATTAGC AGGTTTCTAC      300

TGGCTGATTG CAATTTTAGG TAAAATGCCA GTTTCACTTG GAAATGTATG GCGAATTGTG      360

ACCGCCCTTA TCGGCATACT ATTTATGTAT GTAATGAATC AGGTTTACCA TATTACAAGC      420

ATACCAACTT GGAATAATGC ATTAACCTCT TGGTCATTCT ACCTTACCGT TGTATTAGGT      480

GGATTAACAT TGAGCTATGC GTTATTAATC CCTAATAAAC AACGTGAATA TCAGCTTCAG      540

CATCTGCCAA GTTTATTCGC CATTGGGGTA TCATTGGTCG CAATAGTAGC CATATATCAA      600

GGCTTCAATT TACACAATAT TCACAGTGCT ATTCAAAATG CCGCTGACCT CGTACCAAAT      660

TATGCCAAA TGACCGTAAC TCGCTTATGT TTACTTTCCA TTGTAGCTTT CCTCTTATTC       720

CGAGTGAAAA ACATAGGACT ATTAGGTATT TCCGTTCTAT TAACGTTAGT AGCTGAAGGC      780

ATCGGCCGCG TATTATTTTA TGGATTACAT ATGACTTACG GCATGGCGAT TGGTGGT         837
```

(2) INFORMATION FOR SEQ ID NO:5:

(i) SEQUENCE CHARACTERISTICS:
        (A) LENGTH: 806 amino acids
        (B) TYPE: amino acid
        (C) STRANDEDNESS: single
        (D) TOPOLOGY: linear (xi) SEQUENCE DESCRIPTION: SEQ ID NO:5:

```
Met Ser Asn Phe Asn Gln Ile Ser Arg Arg Asp Phe Val Lys Ala Ser
1               5                   10                  15

Ser Ala Gly Ala Ala Leu Ala Val Ser Asn Leu Thr Leu Pro Phe Asn
            20                  25                  30

Val Met Ala Lys Glu Thr Gln Arg Leu Asn Glu Asn Asn Gln Glu Arg
        35                  40                  45

Ile Val Trp Ser Ala Cys Thr Val Asn Cys Gly Ser Arg Cys Pro Leu
    50                  55                  60

Arg Met His Val Lys Asp Asn Arg Ile Thr Tyr Val Glu Thr Asp Asn
65                  70                  75                  80

Thr Gly Thr Glu Thr Tyr Asn Leu Asp His Gln Val Arg Ala Cys Leu
                85                  90                  95

Arg Gly Arg Ser Met Arg Arg Val Tyr Asn Pro Asp Arg Leu Lys
            100                 105                 110

Tyr Pro Met Lys Arg Ile Gly Lys Arg Gly Glu Gly Lys Phe Lys Arg
        115                 120                 125

Ile Ser Trp Asp Glu Ala Leu Thr Glu Ile Ala Tyr Ala Leu Lys Arg
```

-continued

```
            130                 135                 140
Asn Ile Lys Lys Tyr Gly Asn Glu Ser Ile Tyr Leu Asn Tyr Gly Thr
145                 150                 155                 160
Gly Thr Leu Gly Gly Thr Met Ala Lys Ser Trp Pro Pro Ala Ser Thr
                165                 170                 175
Met Ile Ala Arg Phe Met Asn Cys Ile Gly Gly Tyr Leu Asn His Tyr
                180                 185                 190
Gly Asp Tyr Ser Thr Ala Gln Ile Ala Val Gly Leu Asp Tyr Thr Tyr
                195                 200                 205
Gly Gly Gly Trp Ala Leu Gly Asn Gly Met Ala Asp Ile Glu Asn Thr
        210                 215                 220
Lys Leu Ile Val Leu Phe Gly Asn Asn Pro Ala Glu Thr Arg Met Ser
225                 230                 235                 240
Gly Gly Gly Leu Thr Tyr Cys Ile Glu Gln Ala Lys Ala Arg Ser Asn
                245                 250                 255
Ala Lys Met Ile Ile Ile Asp Pro Arg Tyr Asn Asp Thr Gly Ala Gly
                260                 265                 270
Arg Glu Asp Glu Trp Ile Pro Ile Arg Pro Gly Thr Asp Ala Ala Leu
                275                 280                 285
Val Ala Ala Leu Ala Tyr Val Met Ile Gln Glu Asn Leu Val Asp Gln
                290                 295                 300
Pro Phe Leu Asp Lys Tyr Cys Val Gly Tyr Asp Glu Lys Thr Leu Pro
305                 310                 315                 320
Ala Asp Ala Pro Lys Asn Gly His Tyr Lys Ala Tyr Ile Leu Gly Tyr
                325                 330                 335
Gly Asn Asp Gly Ile Ala Lys Thr Pro Glu Trp Ala Ala Lys Ile Thr
                340                 345                 350
Gly Ile Pro Ala Glu Arg Ile Ile Lys Leu Ala Arg Glu Ile Gly Ser
                355                 360                 365
Thr Lys Pro Ala Phe Ile Ser Gln Gly Trp Gly Pro Gln Arg Arg Ser
        370                 375                 380
Asn Gly Glu Leu Ile Ser Arg Ala Ile Ala Met Leu Pro Ile Leu Thr
385                 390                 395                 400
Gly Asn Val Gly Ile His Gly Gly Asn Thr Gly Ala Arg Glu Ser Ala
                405                 410                 415
Tyr Ser Ile Pro Phe Val Arg Met Pro Thr Leu Lys Asn Pro Met Lys
                420                 425                 430
Ala Ser Ile Pro Met Phe Leu Gly Thr Asp Ala Ile Ile Arg Gly Thr
        435                 440                 445
Glu Met Thr Ala Leu Thr Asp Gly Ile Arg Gly Val Asp Lys Leu Ser
        450                 455                 460
Pro Pro Ile Lys Val Ile Trp Asn Tyr Ala Ser Asn Cys Leu Ile Asn
465                 470                 475                 480
Gln His Ala Gln Ile Asn Arg Thr His Asp Ile Leu Gln Asp Asp Thr
                485                 490                 495
Gln Cys Glu Met Ile Ile Thr Ile Asp Asn His Met Thr Ser Thr Ala
                500                 505                 510
Lys Tyr Ser Asp Ile Leu Leu Pro Asp Cys Pro Thr Ser Glu Gln Met
        515                 520                 525
Asp Phe Ala Leu Asp Ala Phe Val Ser Asn Met Ala Tyr Val Ile Phe
        530                 535                 540
Ala Asp Gln Val Ile Lys Pro Ser Phe Glu Cys Arg Pro Ile Tyr Asp
545                 550                 555                 560
```

```
Met Leu Ser Asp Leu Ala Glu Lys Met Gly Val Lys Glu Lys Phe Thr
                565                 570                 575
Glu Gly Arg Thr Gln Glu Glu Trp Leu Arg His Ile Tyr Glu Gln Ser
            580                 585                 590
Arg Glu Lys Leu Pro Glu Leu Pro Thr Phe Glu Glu Phe Arg Gln Gln
        595                 600                 605
Gly Ile Phe Lys Lys Val Asp Pro Asn Gly Phe Lys Val Ala Tyr Lys
    610                 615                 620
Asp Phe Arg Asp Asn Pro Glu Ala His Pro Leu Lys Thr Pro Ser Gly
625                 630                 635                 640
Lys Ile Glu Ile Tyr Ser Ser Arg Leu Ala Glu Ile Ala Lys Thr Trp
                645                 650                 655
Lys Leu Ala Glu Asp Asp Val Ile His Pro Leu Pro Ile His Ala Gln
            660                 665                 670
Ser Phe Glu His Tyr Gly Asp Pro Leu Met Glu Lys Tyr Pro Leu Gln
        675                 680                 685
Leu Ser Gly Phe His Tyr Lys Ala Arg Thr His Ser Thr Tyr Gly Asn
    690                 695                 700
Val Asp Val Leu Lys Ala Ala Asn Pro Gln Glu Val Trp Met Asn Pro
705                 710                 715                 720
Ile Asp Ala Lys Pro Arg Asn Ile Lys Asn Gly Asp Met Ile Arg Ile
                725                 730                 735
Phe Asn Asp Arg Gly Glu Val His Ile Asn Val Lys Ile Thr Pro Arg
            740                 745                 750
Ile Ile Pro Gly Val Val Ala Leu Ser Glu Gly Ala Trp Tyr Ala Pro
        755                 760                 765
Asp Lys Asp Arg Ile Asp His Ser Gly Cys Ile Asn Val Leu Thr Thr
    770                 775                 780
Gln Arg Pro Ser Pro Leu Ala Lys Gly Asn Pro Gln His Ser Asn Leu
785                 790                 795                 800
Val Gln Val Glu Arg Leu
                805

(2) INFORMATION FOR SEQ ID NO:6:

(i) SEQUENCE CHARACTERISTICS:
        (A) LENGTH: 205 amino acids
        (B) TYPE: amino acid
        (C) STRANDEDNESS: single
        (D) TOPOLOGY: linear (xi) SEQUENCE DESCRIPTION: SEQ ID NO:6:

Met Glu Gln Tyr Gly Phe Tyr Phe Asp Ser Glu Arg Cys Thr Gly Cys
1               5                   10                  15
Lys Thr Cys Glu Leu Ala Cys Lys Asp Tyr Lys Asp Leu Gly Thr Glu
                20                  25                  30
Val Asn Phe Arg Arg Ile Tyr Glu Tyr Thr Gly Gly Gln Trp Asn Gln
            35                  40                  45
Gln Ala Asp Gly Cys Trp His Gln Asn Ile Phe Gly Tyr Tyr Met Ser
        50                  55                  60
Ile Ser Cys Asn His Cys Ala Asp Pro Ala Cys Thr Lys Val Cys Pro
65                  70                  75                  80
Thr Gly Ala Met His Lys Asn Ala Asp Gly Phe Val Ile Val Asn Glu
                85                  90                  95
Glu Ile Cys Ile Gly Cys Arg Tyr Cys His Met Ala Cys Pro Tyr Asp
```

-continued

```
                100                 105                 110
Ala Pro Gln Tyr Asp Ala Gln Lys Gly His Met Thr Lys Cys Asp Gly
            115                 120                 125
Cys Tyr Ser Arg Val Lys Ser Gly Gln Lys Pro Ile Cys Val Asp Ala
130                 135                 140
Cys Pro Leu Arg Ala Leu Asp Phe Ala Pro Ile Asp Glu Leu Arg Thr
145                 150                 155                 160
Lys Tyr Gly Thr Gln Ala Ser Ile Ala Pro Leu Pro Thr Asp Ile
                165                 170                 175
Thr Gln Pro Asn Leu Val Val Lys Pro Asn Lys Tyr Ala Arg Leu Ser
                180                 185                 190
Gly Asp Thr Ser Gly Phe Leu Gly Asn Pro Arg Glu Val
            195                 200                 205
```

(2) INFORMATION FOR SEQ ID NO:7:

(i) SEQUENCE CHARACTERISTICS:
        (A) LENGTH: 279 amino acids
        (B) TYPE: amino acid
        (C) STRANDEDNESS: single
        (D) TOPOLOGY: linear (xi) SEQUENCE DESCRIPTION: SEQ ID NO:7:

```
Met Asn Thr Gly Leu Tyr Glu Leu Pro Leu Val Phe Phe Thr Val Leu
1               5                   10                  15
Ala Gln Ser Ala Ala Gly Ala Trp Leu Val Phe Thr Phe Val Leu Leu
                20                  25                  30
Asn Glu Lys Asn Thr Lys Ser Arg Thr Tyr Ile His Lys Val Met Phe
            35                  40                  45
Val Ile Leu Ala Leu Leu Gly Ile Gly Phe Ile Ala Ser Ile Met His
        50                  55                  60
Leu Gly Leu Pro Ile Arg Ala Phe Asn Ser Leu Asn Arg Val Gly Ser
65                  70                  75                  80
Ser Met Met Ser Asn Glu Ile Ala Ala Gly Ala Ile Phe Phe Thr Leu
                85                  90                  95
Ala Gly Phe Tyr Trp Leu Ile Ala Ile Leu Gly Lys Met Pro Val Ser
                100                 105                 110
Leu Gly Asn Val Trp Arg Ile Val Thr Ala Leu Ile Gly Ile Leu Phe
            115                 120                 125
Met Tyr Val Met Asn Gln Val Tyr His Ile Thr Ser Ile Pro Thr Trp
        130                 135                 140
Asn Asn Ala Leu Thr Ser Trp Ser Phe Tyr Leu Thr Val Val Leu Gly
145                 150                 155                 160
Gly Leu Thr Leu Ser Tyr Ala Leu Leu Ile Pro Asn Lys Gln Arg Glu
                165                 170                 175
Tyr Gln Leu Gln His Leu Pro Ser Leu Phe Ala Ile Gly Val Ser Leu
                180                 185                 190
Val Ala Ile Val Ala Ile Tyr Gln Gly Phe Asn Leu His Asn Ile His
            195                 200                 205
Ser Ala Ile Gln Asn Ala Ala Asp Leu Val Pro Asn Tyr Ala Ile Met
        210                 215                 220
Thr Val Thr Arg Leu Cys Leu Leu Ser Ile Val Ala Phe Leu Leu Phe
225                 230                 235                 240
Arg Val Lys Asn Ile Gly Leu Leu Gly Ile Ser Val Leu Leu Thr Leu
                245                 250                 255
```

Val Ala Glu Gly Ile Gly Arg Val Leu Phe Tyr Gly Leu His Met Thr
            260                 265                 270

Tyr Gly Met Ala Ile Gly Gly
        275

(2) INFORMATION FOR SEQ ID NO:8:

(i) SEQUENCE CHARACTERISTICS:
        (A) LENGTH: 785 amino acids
        (B) TYPE: amino acid
        (C) STRANDEDNESS: single
        (D) TOPOLOGY: linear (xi) SEQUENCE DESCRIPTION: SEQ ID NO:8:

Met Ala Ser Ser Ala Leu Thr Leu Pro Phe Ser Arg Ile Ala His Ala
1               5                   10                  15

Val Asp Ser Ala Ile Pro Thr Lys Ser Asp Glu Lys Val Ile Trp Ser
            20                  25                  30

Ala Cys Thr Val Asn Cys Gly Ser Arg Cys Pro Leu Arg Met His Val
        35                  40                  45

Val Asp Gly Glu Ile Lys Tyr Val Glu Thr Asp Asn Thr Gly Asp Asp
50                  55                  60

Asn Tyr Asp Gly Leu His Gln Val Arg Ala Cys Leu Arg Gly Arg Ser
65                  70                  75                  80

Met Arg Arg Arg Val Tyr Asn Pro Asp Arg Leu Lys Tyr Pro Met Lys
                85                  90                  95

Arg Val Gly Ala Arg Gly Glu Gly Lys Phe Glu Arg Ile Ser Trp Glu
            100                 105                 110

Glu Ala Tyr Asp Ile Ile Ala Thr Asn Met Gln Arg Leu Ile Lys Glu
        115                 120                 125

Tyr Gly Asn Glu Ser Ile Tyr Leu Asn Tyr Gly Thr Gly Thr Leu Gly
130                 135                 140

Gly Thr Met Thr Arg Ser Trp Pro Pro Gly Asn Thr Leu Val Ala Arg
145                 150                 155                 160

Leu Met Asn Cys Cys Gly Gly Tyr Leu Asn His Tyr Gly Asp Tyr Ser
                165                 170                 175

Ser Ala Gln Ile Ala Glu Gly Leu Asn Tyr Thr Tyr Gly Gly Trp Ala
            180                 185                 190

Asp Gly Asn Ser Pro Ser Asp Ile Glu Asn Ser Lys Leu Val Val Leu
        195                 200                 205

Phe Gly Asn Asn Pro Gly Glu Thr Arg Met Ser Gly Gly Gly Val Thr
210                 215                 220

Tyr Tyr Leu Glu Gln Ala Arg Gln Lys Ser Asn Ala Arg Met Ile Ile
225                 230                 235                 240

Ile Asp Pro Arg Tyr Thr Asp Thr Gly Ala Gly Arg Glu Asp Glu Trp
                245                 250                 255

Ile Pro Ile Arg Pro Gly Thr Asp Ala Ala Leu Val Asn Gly Leu Ala
            260                 265                 270

Tyr Val Met Ile Thr Glu Asn Leu Val Asp Gln Ala Phe Leu Asp Lys
        275                 280                 285

Tyr Cys Val Gly Tyr Asp Glu Lys Thr Leu Pro Ala Ser Ala Pro Lys
290                 295                 300

Asn Gly His Tyr Lys Ala Tyr Ile Leu Gly Glu Gly Pro Asp Gly Val
305                 310                 315                 320

Ala Lys Thr Pro Glu Trp Ala Ser Gln Ile Thr Gly Val Pro Ala Asp
                325                 330                 335

-continued

```
Lys Ile Ile Lys Leu Ala Arg Glu Ile Gly Ser Thr Lys Pro Ala Phe
            340                 345                 350

Ile Ser Gln Gly Trp Gly Pro Gln Arg His Ala Asn Gly Glu Ile Ala
            355                 360                 365

Thr Arg Ala Ile Ser Met Leu Ala Ile Leu Thr Gly Asn Val Gly Ile
            370                 375                 380

Asn Gly Gly Asn Ser Gly Ala Arg Glu Gly Ser Tyr Ser Leu Pro Phe
385                 390                 395                 400

Val Arg Met Pro Thr Leu Glu Asn Pro Ile Gln Thr Ser Ile Ser Met
            405                 410                 415

Phe Met Trp Thr Asp Ala Ile Glu Arg Gly Pro Glu Met Thr Ala Leu
            420                 425                 430

Arg Asp Gly Val Arg Gly Lys Asp Lys Leu Asp Val Pro Ile Lys Met
            435                 440                 445

Ile Trp Asn Tyr Ala Gly Asn Cys Leu Ile Asn Gln His Ser Glu Ile
            450                 455                 460

Asn Arg Thr His Glu Ile Leu Gln Asp Asp Lys Lys Cys Glu Leu Ile
465                 470                 475                 480

Val Val Ile Asp Cys His Met Thr Ser Ser Ala Lys Tyr Ala Asp Ile
            485                 490                 495

Leu Leu Pro Asp Cys Thr Ala Ser Glu Gln Met Asp Phe Ala Leu Asp
            500                 505                 510

Ala Ser Cys Gly Asn Met Ser Tyr Val Ile Phe Asn Asp Gln Val Ile
            515                 520                 525

Lys Pro Arg Phe Glu Cys Lys Thr Ile Tyr Glu Met Thr Ser Glu Leu
            530                 535                 540

Ala Lys Arg Leu Gly Val Glu Gln Gln Phe Thr Gly Arg Thr Gln
545                 550                 555                 560

Glu Glu Trp Met Arg His Leu Tyr Ala Gln Ser Arg Glu Ala Ile Pro
            565                 570                 575

Glu Leu Pro Thr Phe Glu Glu Phe Arg Lys Gln Gly Ile Phe Lys Lys
            580                 585                 590

Arg Asp Pro Gln Gly His His Val Ala Tyr Lys Ala Phe Arg Glu Asp
            595                 600                 605

Pro Gln Ala Asn Pro Leu Thr Thr Pro Ser Gly Lys Ile Glu Ile Tyr
            610                 615                 620

Ser Gln Ala Leu Ala Asp Ile Ala Ala Thr Trp Glu Leu Pro Glu Gly
625                 630                 635                 640

Asp Val Ile Asp Pro Leu Pro Ile Tyr Thr Pro Gly Phe Glu Ser Tyr
            645                 650                 655

Gln Asp Pro Leu Asn Lys Gln Tyr Pro Leu Gln Leu Thr Gly Phe His
            660                 665                 670

Tyr Lys Ser Arg Val His Ser Thr Tyr Gly Asn Val Asp Val Leu Lys
            675                 680                 685

Ala Ala Cys Arg Gln Glu Met Trp Ile Asn Pro Leu Asp Ala Gln Lys
            690                 695                 700

Arg Gly Ile His Asn Gly Asp Lys Val Arg Ile Phe Asn Asp Arg Gly
705                 710                 715                 720

Glu Val His Ile Glu Ala Lys Val Thr Pro Arg Met Met Pro Gly Val
            725                 730                 735

Val Ala Leu Gly Glu Gly Ala Trp Tyr Asp Pro Asp Ala Lys Arg Val
            740                 745                 750
```

-continued

```
Asp Lys Gly Gly Cys Ile Asn Val Leu Thr Thr Gln Arg Pro Ser Pro
        755                 760                 765

Leu Ala Lys Gly Asn Pro Ser His Thr Asn Leu Val Gln Val Glu Lys
        770                 775                 780

Val
785
```

(2) INFORMATION FOR SEQ ID NO:9:

(i) SEQUENCE CHARACTERISTICS:
        (A) LENGTH: 207 amino acids
        (B) TYPE: amino acid
        (C) STRANDEDNESS: single
        (D) TOPOLOGY: linear (xi) SEQUENCE DESCRIPTION: SEQ ID NO:9:

```
Met Thr Thr Gln Tyr Gly Phe Phe Ile Asp Ser Ser Arg Cys Thr Gly
1               5                   10                  15

Cys Lys Thr Cys Glu Leu Ala Cys Lys Asp Tyr Lys Asp Leu Thr Pro
            20                  25                  30

Glu Val Ser Phe Arg Arg Ile Tyr Glu Tyr Ala Gly Gly Asp Trp Gln
        35                  40                  45

Glu Asp Asn Gly Val Trp His Gln Asn Val Phe Ala Tyr Tyr Leu Ser
    50                  55                  60

Ile Ser Cys Asn His Cys Glu Asp Pro Ala Cys Thr Lys Val Cys Pro
65                  70                  75                  80

Ser Gly Ala Met His Lys Arg Glu Asp Gly Phe Val Val Asp Glu
                85                  90                  95

Asp Val Cys Ile Gly Cys Arg Tyr Cys His Met Ala Cys Pro Tyr Gly
                100                 105                 110

Ala Pro Gln Tyr Asn Glu Thr Lys Gly His Met Thr Lys Cys Asp Gly
        115                 120                 125

Cys Tyr Asp Arg Val Ala Glu Gly Lys Lys Pro Ile Cys Val Glu Ser
130                 135                 140

Cys Pro Leu Arg Ala Leu Asp Phe Gly Pro Ile Asp Glu Leu Arg Lys
145                 150                 155                 160

Lys His Gly Asp Leu Ala Ala Val Ala Pro Arg Ala Leu Pro Arg Ala
                165                 170                 175

His Phe Thr Lys Pro Asn Ile Val Ile Lys Pro Asn Ala Asn Ser Arg
                180                 185                 190

Pro Thr Gly Asp Thr Thr Gly Tyr Leu Ala Asn Pro Lys Glu Val
        195                 200                 205
```

(2) INFORMATION FOR SEQ ID NO:10:

(i) SEQUENCE CHARACTERISTICS:
        (A) LENGTH: 287 amino acids
        (B) TYPE: amino acid
        (C) STRANDEDNESS: single
        (D) TOPOLOGY: linear (xi) SEQUENCE DESCRIPTION: SEQ ID NO:10:

```
Met Gly Ser Gly Trp His Glu Trp Pro Leu Met Ile Phe Thr Val Phe
1               5                   10                  15

Gly Gln Cys Val Ala Gly Gly Phe Ile Val Leu Ala Leu Ala Leu Leu
            20                  25                  30

Lys Gly Asp Leu Arg Ala Glu Ala Gln Gln Arg Val Ile Ala Cys Met
        35                  40                  45
```

-continued

```
Phe Gly Leu Trp Val Leu Met Gly Ile Gly Phe Ile Ala Ser Met Leu
 50                  55                  60
His Leu Gly Ser Pro Met Arg Ala Phe Asn Ser Leu Asn Arg Val Gly
 65                  70                  75                  80
Ala Ser Ala Leu Ser Asn Glu Ile Ala Ser Gly Ser Ile Phe Phe Ala
                 85                  90                  95
Val Gly Gly Ile Gly Trp Leu Leu Ala Met Leu Lys Lys Leu Ser Pro
            100                 105                 110
Ala Leu Arg Thr Leu Trp Leu Ile Val Thr Met Val Leu Gly Val Ile
            115                 120                 125
Phe Val Trp Met Met Val Arg Val Tyr Asn Ser Ile Asp Thr Val Pro
            130                 135                 140
Thr Trp Tyr Ser Ile Trp Thr Pro Met Gly Phe Leu Thr Met Phe
145                 150                 155                 160
Met Gly Gly Pro Leu Leu Gly Tyr Leu Leu Ser Leu Ala Gly Val
                165                 170                 175
Asp Gly Trp Ala Met Arg Leu Leu Pro Ala Ile Ser Val Leu Ala Leu
            180                 185                 190
Val Val Ser Gly Val Val Ser Val Met Gln Gly Ala Glu Leu Ala Thr
            195                 200                 205
Ile His Ser Ser Val Gln Gln Ala Ala Ala Leu Val Pro Asp Tyr Gly
            210                 215                 220
Ala Leu Met Ser Trp Arg Ile Val Leu Leu Ala Val Ala Leu Cys Leu
225                 230                 235                 240
Trp Ile Ala Pro Gln Leu Lys Gly Tyr Gln Pro Ala Val Pro Leu Leu
                245                 250                 255
Ser Val Ser Phe Ile Leu Leu Leu Ala Gly Glu Leu Ile Gly Arg Gly
            260                 265                 270
Val Phe Tyr Gly Leu His Met Thr Tyr Gly Met Ala Val Ala Ser
            275                 280                 285

(2) INFORMATION FOR SEQ ID NO:11:

(i) SEQUENCE CHARACTERISTICS:
        (A) LENGTH: 806 amino acids
        (B) TYPE: amino acid
        (C) STRANDEDNESS: single
        (D) TOPOLOGY: linear (xi) SEQUENCE DESCRIPTION: SEQ ID NO:11:

Met Ser Asn Phe Asn Gln Ile Ser Arg Arg Asp Phe Val Lys Ala Ser
 1               5                  10                  15
Ser Ala Gly Ala Ala Leu Ala Val Ser Asn Leu Thr Leu Pro Phe Asn
                 20                  25                  30
Val Met Ala Lys Glu Thr Gln Arg Leu Asn Glu Asn Asn Gln Glu Arg
            35                  40                  45
Ile Val Trp Ser Ala Cys Thr Val Asn Cys Gly Ser Arg Cys Pro Leu
 50                  55                  60
Arg Met His Val Lys Asp Asn Arg Ile Thr Tyr Val Glu Thr Asp Asn
 65                  70                  75                  80
Thr Gly Thr Glu Thr Tyr Asn Leu Asp His Gln Val Arg Ala Cys Leu
                 85                  90                  95
Arg Gly Arg Ser Met Arg Arg Val Tyr Asn Pro Asp Arg Leu Lys
            100                 105                 110
Tyr Pro Met Lys Arg Ile Gly Lys Arg Gly Glu Gly Lys Phe Lys Arg
            115                 120                 125
```

```
Ile Ser Trp Asp Glu Ala Leu Thr Glu Ile Ala Tyr Ala Leu Lys Arg
130                 135                 140

Asn Ile Lys Lys Tyr Gly Asn Glu Ser Ile Tyr Leu Asn Tyr Gly Thr
145                 150                 155                 160

Gly Thr Leu Gly Gly Thr Met Ala Lys Ser Trp Pro Ala Ser Thr
                165                 170                 175

Met Ile Ala Arg Phe Met Asn Cys Ile Gly Gly Tyr Leu Asn His Tyr
            180                 185                 190

Gly Asp Tyr Ser Thr Ala Gln Ile Ala Val Gly Leu Asp Tyr Thr Tyr
        195                 200                 205

Gly Gly Gly Trp Ala Leu Gly Asn Gly Met Ala Asp Ile Glu Asn Thr
    210                 215                 220

Lys Leu Ile Val Leu Phe Gly Asn Asn Pro Ala Glu Thr Arg Met Ser
225                 230                 235                 240

Gly Gly Gly Leu Thr Tyr Cys Ile Glu Gln Ala Lys Ala Arg Ser Asn
                245                 250                 255

Ala Lys Met Ile Ile Ile Asp Pro Arg Tyr Asn Asp Thr Gly Ala Gly
            260                 265                 270

Arg Glu Asp Glu Trp Ile Pro Ile Arg Pro Gly Thr Asp Ala Ala Leu
        275                 280                 285

Val Ala Ala Leu Ala Tyr Val Met Ile Gln Glu Asn Leu Val Asp Gln
    290                 295                 300

Pro Phe Leu Asp Lys Tyr Cys Val Gly Tyr Asp Glu Lys Thr Leu Pro
305                 310                 315                 320

Ala Asp Ala Pro Lys Asn Gly His Tyr Lys Ala Tyr Ile Leu Gly Tyr
                325                 330                 335

Gly Asn Asp Gly Ile Ala Lys Thr Pro Glu Trp Ala Ala Lys Ile Thr
            340                 345                 350

Gly Ile Pro Ala Glu Arg Ile Lys Leu Ala Arg Glu Ile Gly Ser
        355                 360                 365

Thr Lys Pro Ala Phe Ile Ser Gln Gly Trp Gly Pro Gln Arg Arg Ser
    370                 375                 380

Asn Gly Glu Leu Ile Ser Arg Ala Ile Ala Met Leu Pro Ile Leu Thr
385                 390                 395                 400

Gly Asn Val Gly Ile His Gly Gly Asn Thr Gly Ala Arg Glu Ser Ala
                405                 410                 415

Tyr Ser Ile Pro Phe Val Arg Met Pro Thr Leu Lys Asn Pro Met Lys
            420                 425                 430

Ala Ser Ile Pro Met Phe Leu Gly Thr Asp Ala Ile Ile Arg Gly Thr
        435                 440                 445

Glu Met Thr Ala Leu Thr Asp Gly Ile Arg Gly Val Asp Lys Leu Ser
    450                 455                 460

Pro Pro Ile Lys Val Ile Trp Asn Tyr Ala Ser Asn Cys Leu Ile Asn
465                 470                 475                 480

Gln His Ala Gln Ile Asn Arg Thr His Asp Ile Leu Gln Asp Asp Thr
                485                 490                 495

Gln Cys Glu Met Ile Ile Thr Ile Asp Asn His Met Thr Ser Thr Ala
            500                 505                 510

Lys Tyr Ser Asp Ile Leu Leu Pro Asp Cys Pro Thr Ser Glu Gln Met
        515                 520                 525

Asp Phe Ala Leu Asp Ala Phe Val Ser Asn Met Ala Tyr Val Ile Phe
    530                 535                 540
```

```
Ala Asp Gln Val Ile Lys Pro Ser Phe Glu Cys Arg Pro Ile Tyr Asp
545                 550                 555                 560

Met Leu Ser Asp Leu Ala Glu Lys Met Gly Val Lys Glu Lys Phe Thr
            565                 570                 575

Glu Gly Arg Thr Gln Glu Glu Trp Leu Arg His Ile Tyr Glu Gln Ser
            580                 585                 590

Arg Glu Lys Leu Pro Glu Leu Pro Thr Phe Glu Phe Arg Gln Gln
            595                 600                 605

Gly Ile Phe Lys Lys Val Asp Pro Asn Gly Phe Lys Val Ala Tyr Lys
            610                 615                 620

Asp Phe Arg Asp Asn Pro Glu Ala His Pro Leu Lys Thr Pro Ser Gly
625                 630                 635                 640

Lys Ile Glu Ile Tyr Ser Ser Arg Leu Ala Glu Ile Ala Lys Thr Trp
            645                 650                 655

Lys Leu Ala Glu Asp Asp Val Ile His Pro Leu Pro Ile His Ala Gln
            660                 665                 670

Ser Phe Glu His Tyr Gly Asp Pro Leu Met Glu Lys Tyr Pro Leu Gln
            675                 680                 685

Leu Ser Gly Phe His Tyr Lys Ala Arg Thr His Ser Thr Tyr Gly Asn
690                 695                 700

Val Asp Val Leu Lys Ala Ala Asn Pro Gln Glu Val Trp Met Asn Pro
705                 710                 715                 720

Ile Asp Ala Lys Pro Arg Asn Ile Lys Asn Gly Asp Met Ile Arg Ile
            725                 730                 735

Phe Asn Asp Arg Gly Glu Val His Ile Asn Val Lys Ile Thr Pro Arg
            740                 745                 750

Ile Ile Pro Gly Val Val Ala Leu Ser Glu Gly Ala Trp Tyr Ala Pro
            755                 760                 765

Asp Lys Asp Arg Ile Asp His Ser Gly Cys Ile Asn Val Leu Thr Thr
            770                 775                 780

Gln Arg Pro Ser Pro Leu Ala Lys Gly Asn Pro Gln His Ser Asn Leu
785                 790                 795                 800

Val Gln Val Glu Arg Leu
                805

(2) INFORMATION FOR SEQ ID NO:12:

(i) SEQUENCE CHARACTERISTICS:
        (A) LENGTH: 205 amino acids
        (B) TYPE: amino acid
        (C) STRANDEDNESS: single
        (D) TOPOLOGY: linear (xi) SEQUENCE DESCRIPTION: SEQ ID NO:12:

Met Glu Gln Tyr Gly Phe Tyr Phe Asp Ser Glu Arg Cys Thr Gly Cys
1               5                   10                  15

Lys Thr Cys Glu Leu Ala Cys Lys Asp Tyr Lys Asp Leu Gly Thr Glu
                20                  25                  30

Val Asn Phe Arg Arg Ile Tyr Glu Tyr Thr Gly Gly Gln Trp Asn Gln
            35                  40                  45

Gln Ala Asp Gly Cys Trp His Gln Asn Ile Phe Gly Tyr Tyr Met Ser
50                  55                  60

Ile Ser Cys Asn His Cys Ala Asp Pro Ala Cys Thr Lys Val Cys Pro
65                  70                  75                  80

Thr Gly Ala Met His Lys Asn Ala Asp Gly Phe Val Ile Val Asn Glu
            85                  90                  95
```

-continued

```
Glu Ile Cys Ile Gly Cys Arg Tyr Cys His Met Ala Cys Pro Tyr Asp
            100                 105                 110

Ala Pro Gln Tyr Asp Ala Gln Lys Gly His Met Thr Lys Cys Asp Gly
        115                 120                 125

Cys Tyr Ser Arg Val Lys Ser Gly Gln Lys Pro Ile Cys Val Asp Ala
    130                 135                 140

Cys Pro Leu Arg Ala Leu Asp Phe Ala Pro Ile Asp Glu Leu Arg Thr
145                 150                 155                 160

Lys Tyr Gly Thr Gln Ala Ser Ile Ala Pro Leu Pro Pro Thr Asp Ile
                165                 170                 175

Thr Gln Pro Asn Leu Val Val Lys Pro Asn Lys Tyr Ala Arg Leu Ser
            180                 185                 190

Gly Asp Thr Ser Gly Phe Leu Gly Asn Pro Arg Glu Val
            195                 200                 205
```